US012011500B2

(12) United States Patent
Lebreton et al.

(10) Patent No.: US 12,011,500 B2
(45) Date of Patent: *Jun. 18, 2024

(54) COMPOSITIONS AND METHODS FOR IMPROVING SKIN APPEARANCE

(71) Applicant: Allergan Industrie, SAS, Pringy (FR)

(72) Inventors: Pierre Lebreton, Annecy (FR); Olivier Guetta, Annecy (FR)

(73) Assignee: Allergan Industrie, SAS, Pringy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/684,248

(22) Filed: Mar. 1, 2022

(65) Prior Publication Data
US 2022/0257495 A1 Aug. 18, 2022

Related U.S. Application Data

(60) Continuation of application No. 16/877,315, filed on May 18, 2020, now Pat. No. 11,260,015, which is a division of application No. 15/549,990, filed as application No. PCT/EP2016/052682 on Feb. 9, 2016, now abandoned.

(30) Foreign Application Priority Data

Feb. 9, 2015 (WO) ................. PCT/IB2015/000347

(51) Int. Cl.
A61Q 19/00 (2006.01)
A61K 8/04 (2006.01)
A61K 8/34 (2006.01)
A61K 8/42 (2006.01)
A61K 8/67 (2006.01)
A61K 8/73 (2006.01)
A61Q 19/08 (2006.01)

(52) U.S. Cl.
CPC .............. *A61K 8/735* (2013.01); *A61K 8/042* (2013.01); *A61K 8/345* (2013.01); *A61K 8/42* (2013.01); *A61K 8/676* (2013.01); *A61Q 19/00* (2013.01); *A61Q 19/08* (2013.01); *A61K 2800/91* (2013.01)

(58) Field of Classification Search
CPC ......... A61Q 19/00; A61Q 19/08; A61P 17/00; C08B 37/0072
See application file for complete search history.

(56) References Cited

U.S. PATENT DOCUMENTS

| | | |
|---|---|---|
| 2,128,827 A | 8/1938 | Killian |
| 3,548,056 A | 12/1970 | Eigen et al. |
| 3,763,009 A | 10/1973 | Suzuki et al. |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs et al. |
| 4,642,117 A | 2/1987 | Nguyen et al. |
| 4,713,448 A | 12/1987 | Balazs et al. |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,492,936 A | 2/1996 | Francese et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto et al. |

(Continued)

FOREIGN PATENT DOCUMENTS

| | | |
|---|---|---|
| CA | 949965 | 6/1974 |
| CN | 104105474 | 10/2014 |

(Continued)

OTHER PUBLICATIONS

A Clinician's Guide to the 8-Point Lift. Vycross Collection. Juvéderm. Volbella Volift Voluma with Lidocaine. (May 2014). [Brochure]. Allergan. 13 pages.
EP 3256097 Communication of a Notice of Opposition, Allergan Industrie SAS, 198 354 aa_sis, Oct. 11, 2022, 1 page.
EP 3256097 Notice of Opposition, Opponent: Laboratories Vivacy, Oct. 5, 2022, 22 pages. [English language translation].
EP 3256097 Notice of Opposition and Opposition, Opponent: Laboratories Vivacy, Oct. 5, 2022, 30 pages. [French language].
EP 3256097 Notice of Opposition and Opposition, Opponent: Merz Pharma GmbH & Co. KGaA, Oct. 5, 2022, 18 pages.
Faivre, J. et al. (May 2021). "Advanced Concepts in Rheology for the Evaluation of Hyaluronic Acid-Based Soft Tissue Fillers." Dermatologic Surgery 47(5):p. e159-e167.

(Continued)

*Primary Examiner* — Pancham Bakshi
(74) *Attorney, Agent, or Firm* — Mintz, Levin, Cohn, Ferris, Glovsky and Popeo, P.C.

(57) ABSTRACT

Injectable compositions and methods of treating skin can help improve hydration, elasticity and/or texture of the skin. The compositions can be based on crosslinked hyaluronic acid matrices made with low molecular weight hyaluronic acids.

28 Claims, 5 Drawing Sheets

(56) References Cited

U.S. PATENT DOCUMENTS

| | | |
|---|---|---|
| 5,616,689 A | 4/1997 | Shenoy et al. |
| 5,633,001 A | 5/1997 | Bengt Agerup |
| 5,643,464 A | 7/1997 | Rhee et al. |
| 5,676,964 A | 10/1997 | Della Valle et al. |
| 5,823,671 A | 10/1998 | Mitchell et al. |
| 5,824,333 A | 10/1998 | Scopelianos et al. |
| 5,827,529 A | 10/1998 | Ono et al. |
| 5,827,937 A | 10/1998 | Agerup |
| 5,843,907 A | 12/1998 | Sakai et al. |
| 5,880,107 A | 3/1999 | Buenter |
| 5,886,042 A | 3/1999 | Yu et al. |
| 5,935,164 A | 8/1999 | Iversen |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,586,493 B1 | 7/2003 | Massia et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci et al. |
| 6,767,924 B2 | 7/2004 | Yu et al. |
| 6,767,928 B1 | 7/2004 | Murphy et al. |
| 6,852,255 B2 | 2/2005 | Yang et al. |
| 6,893,466 B2 | 5/2005 | Trieu |
| 6,903,199 B2 | 6/2005 | Moon et al. |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg et al. |
| 7,196,180 B2 | 3/2007 | Aeschlimann et al. |
| 7,314,636 B2 | 1/2008 | Caseres et al. |
| 7,491,709 B2 | 2/2009 | Carey |
| 7,741,476 B2 | 6/2010 | Lebreton |
| 7,902,171 B2 | 3/2011 | Reinmuller et al. |
| 8,124,120 B2 | 2/2012 | Sadozai et al. |
| 9,393,263 B2 * | 7/2016 | Liu .................. A61K 8/676 |
| 9,898,263 B2 | 2/2018 | Zhang |
| 11,260,015 B2 * | 3/2022 | Lebreton ............... A61Q 19/00 |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter et al. |
| 2005/0186261 A1 | 8/2005 | Avelar et al. |
| 2005/0186673 A1 | 8/2005 | Geistlich et al. |
| 2005/0226936 A1 | 10/2005 | Agerup |
| 2005/0271729 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang et al. |
| 2006/0194758 A1 | 8/2006 | Lebreton et al. |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik et al. |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui et al. |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons et al. |
| 2008/0268051 A1 | 10/2008 | Hughes et al. |
| 2008/0274946 A1 | 11/2008 | Giampapa |
| 2008/0279806 A1 | 11/2008 | Cho |
| 2009/0018102 A1 | 1/2009 | Moutet et al. |
| 2009/0022808 A1 | 1/2009 | Champion et al. |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel et al. |
| 2009/0148527 A1 | 6/2009 | Robinson et al. |
| 2009/0155314 A1 | 6/2009 | Tezel et al. |
| 2009/0155362 A1 | 6/2009 | Longin et al. |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0316683 A1 | 12/2010 | Piron et al. |
| 2011/0034684 A1 | 2/2011 | Yokokawa et al. |
| 2011/0118206 A1 | 5/2011 | Lebreton |
| 2011/0172180 A1 | 7/2011 | Gousse |
| 2012/0208890 A1 | 8/2012 | Gousse |
| 2013/0203696 A1 | 8/2013 | Njikang et al. |
| 2013/0210760 A1 * | 8/2013 | Liu .................. A61K 8/676 |
| | | 514/54 |
| 2014/0011990 A1 | 1/2014 | Lebreton |

FOREIGN PATENT DOCUMENTS

| | | |
|---|---|---|
| EP | 0273823 | 7/1988 |
| EP | 0416250 | 3/1991 |
| EP | 0416846 | 3/1991 |
| EP | 1247522 | 10/2002 |
| EP | 1398131 | 3/2004 |
| EP | 1419792 | 5/2004 |
| EP | 1532991 | 5/2005 |
| EP | 1726299 | 11/2006 |
| EP | 2236523 | 6/2010 |
| FR | 2733427 | 10/1996 |
| FR | 2759576 | 8/1999 |
| FR | 2759577 | 8/1999 |
| FR | 2780730 | 1/2000 |
| FR | 2920000 | 2/2009 |

(56) References Cited

FOREIGN PATENT DOCUMENTS

| | | |
|---|---|---|
| FR | 2924615 | 6/2009 |
| JP | S 55-0153711 | 11/1980 |
| JP | H 7-163655 | 6/1995 |
| JP | 2007-063177 | 3/2007 |
| JP | 2014-504623 A | 2/2014 |
| KR | 20140072008 A | 6/2014 |
| RU | 2477138 | 3/2013 |
| WO | WO 86/000079 | 1/1986 |
| WO | WO 86/000912 | 2/1986 |
| WO | WO 92/000105 | 1/1992 |
| WO | WO 92/020349 | 11/1992 |
| WO | WO 96/033751 | 10/1993 |
| WO | WO 94/001468 | 1/1994 |
| WO | WO 94/002517 | 3/1994 |
| WO | WO 94/09795 | 5/1994 |
| WO | WO 97/004012 | 6/1997 |
| WO | WO 98/035639 | 8/1998 |
| WO | WO 98/035640 | 8/1998 |
| WO | WO 00/001428 | 1/2000 |
| WO | WO 01/079342 | 10/2001 |
| WO | WO 02/005753 | 1/2002 |
| WO | WO 02/006350 | 1/2002 |
| WO | WO 02/009792 | 2/2002 |
| WO | WO 03/007782 | 1/2003 |
| WO | WO 02/017713 | 3/2003 |
| WO | WO 2004/020473 | 3/2004 |
| WO | WO 2004/022603 | 3/2004 |
| WO | WO 2004/073759 | 9/2004 |
| WO | WO 2004/092222 | 10/2004 |
| WO | WO 2004/092223 | 10/2004 |
| WO | WO 2005/040224 | 6/2005 |
| WO | WO 2005/067944 | 7/2005 |
| WO | WO 2005/067994 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2008/034176 | 3/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO 2008/157608 | 12/2008 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/015901 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |
| WO | WO-2011/086458 A1 | 7/2011 |
| WO | WO-2012/062775 A1 | 5/2012 |
| WO | WO 2013/040242 | 3/2013 |
| WO | WO-2014/198406 A1 | 12/2014 |

OTHER PUBLICATIONS

Juvéderm Volbella with Lidocaine. (Jan. 23, 2013) [Brochure]. Allergan. 9 pages.

Kasten, R. MD, Schmidt, S. MD. (Nov. 2014). Volumisierung des Mittelgesichts. Face: interdisziplinares magazin fur asthetik, 4, 10-14. 6 pages. [German language].

Kasten, R. MD, Schmidt, S. Md. (Nov. 2014). Volumization of the Midface [Google trans.]. [Face: Interdisciplinary Magazine for Aesthetics,] 4, 10-14. 5 pages. [English language].

R&D Curriculum Vitae of Sebastien Pierre, Ph.D., Research Manager, Sr.

Restylane® Skinboosters (Vital & Lip Refresh). (2014) Consulting Room. Retrieved from http://www.consultingroom.com:80/treatments/restylane-vital Archived at https://web.archive.org/web/20141027085754. 4 pages.

Reuther, T. et al. (2010). "Effects of a three-session skin rejuvenation treatment using stabilized hyaluronic acid-based gel of non-animal origin on skin elasticity: a pilot study." Archives of Dermatological Research, 302(1), 37-45.

Scegli Juvéderm. (2019). Catalogo prodotti completo. [Product Catalog]. Allergan. 11 pages. [Italian language].

Scegli Juvéderm. (2019). Catalogue de produits complet. [Product Catalog]. Allergan. 11 pages. [Google Trans. French language].

Shu et al. "In situ crosslinkable hyaluronan hydrogels for tissue engineering." Biomaterials, 25, (7-8): 1339-1348. (2004).

Sivagnanam, G. (2010). "Mesotherapy—The french connection." Journal of Pharmacology & Pharmacotherapeutics, 1(1), 4-8.

Third Party Observation from EP 2637710, dated Aug. 26, 2015.

Third Party Observation from EP 2637710, dated Feb. 1, 2016.

Varioderm Mesolift. (Sep. 2, 2013). Recherche Google. [Google search results]. Adoderm. 2 pages.

Varioderm Mesolift. (Feb. 9, 2013). [Product sheet]. Adoderm. https://adoderm.It/en/varioderm-mesolift1. 1 page.

Varioderm: Soin Du Visage El Arte Del Rejuvenecimiento. (Dec. 31, 2011). [Brochure]. Adoderm. 16 pages. [Google Trans. French language].

Tomasello, "Juvederm Voluma for Cheek Enhancement | ClearSkinMD.net," Mar. 2016, retrieved from https://www.clearskinmd.net/juvederm/.

"Juvederm family of products," Jun. 2015, 2 pages, retrieved from https://nebula.wsimg.com/b27e85012bd5e8924a6a745fd990f753?AccessKeyId=854699786DC957AB88BF&disposition=0.

"The European Aesthetic Guide," Dec. 2011, retrieved from http://cdn.coverstand.com/3708/63217/63217.5.pdf.

Adams, "An Analysis of Clinical Studies of the Use of Crosslinked Hyaluronan, Hylan, in the Treatment of Osteoarthritis," The Journal of Rheumatology, 1993, 16-18, 20 (39).

Aesthetic Buyers Guide, Juvederm Raises Standards, 2007, 1, 4-7; www.miinews.com.

Albano et al., "Hydroxyethyl Radicals in Ethanol Hepatotoxicity," Frontiers in Bioscience, 1999, 533-540, 4.

Allemann, "Hyaluronic Acid Gel (Juvederm) Preparations in the Treatment of Facial Wrinkles and Folds," Clinical Interventions in Aging, 2008, 629-634, 3 (4).

Alsoufi, New and Innovative Developments in Hyaluronic Acid Fillers for Lip Enhancement and Contouring, European Dermaltology, 2011, vol. 5, pp. 50-53.

Antunes et al., "Efficacy of Intrarectal Lidocaine Hydrochloride Gel for Pain Control in Patients Undergoing Transrectal Prostate Biopsy," Clinical Urology, 2004, 380-383, 30.

Atanassoff et al., "The Effect of Intradermal Administration of Lidocaine and Morphine on the Response to Thermal Stimulation," Anesth Analg, 1997, 1340-1343, 84.

Baumann et al., "Comparison of Smooth-Gel Hyaluronic Acid Dermal Fillers with Cross-linked Bovine Collagen: A Multicenter, Double-Masked, Randomized, Within-Subject Study," Dermatologic Surgery, 2007, S128-135, 33 (2).

Beasley et al., "Hyaluronic Acid Fillers: A Comprehensive Review," Facial Plastic Surgery, 2009, 86-94, 25 (2).

Beer, "Dermal Fillers and Combinations of Fillers for Facial Rejuvenation," Dermatologic Clin, 2009, 427-432, 27 (4).

Belda et al., "Hyaluronic Acid Combined With Mannitol to Improve Protection Against Free-Radical Endothelial Damage: Experimental Model," J Cataract Refract Surg, 2005, 1213-1218, 31.

(56) References Cited

OTHER PUBLICATIONS

Bircher et al., "Delayed-type Hypersensitivity to Subcutaneous Lidocaine With Tolerance to Articaine: Confirmation by In Vivo and In Vitro Tests," Contact Dermatitis, 1996, 387-389, 34.
Bluel et al., "Evaluation of Reconstituted Collagen Tape as a Model for Chemically Modified Soft Tissues," Biomat. Med. Dev. Art. Org., 1981, 37-46, 9 (1).
Buck, "Injectable Fillers for Facial Rejuvenation: A Review," Journal of Plastic, Reconstructive & Aesthetic Surgery, 2009, 11-18, 62.
Capozzi et al., "Distant Migration of Silicone Gel From a Ruptured Breast Implant," Silicone Gel Migration, 1978, 302-3, 62 (2).
Carlin, et al., "Effect of Anti-Inflammatory Drugs on Xanthine Oxidase and Xanthine Oxidase Induced Depolymerization of Hyaluronic Acid," Agents and Actions, 1985, 377-384, 16 (5).
Carruthers et al., "The Science and Art of Dermal Fillers for Soft-Tissue Augmentation," Journal of Drugs in Dermatology, 2009, 335-350, 8 (4).
Cavallini et al., "Skin Quality Improvement With VYC-12, a New Injectable Hyaluronic Acid: Objective Results Using Digital Analysis," Dermatol Surg, 2019, 45:1598-1604.
Champion et al., "Role of Target Geometry in Phagocytosis," Proc. Nat. Acad. Sci., 2006, 4930-4934, 103 (13).
Chee, "Estimation of Molecular Weight Averages from Intrinsic Viscosity," Journal of Applied Polymer Science, 1985, 1359-1360, vol. 30, John Wiley & Sons, Inc.
Chin et al., "Allergic Hypersensitivity to Lidocaine Hydrochloride," International Society of Tropical Dermatology, 1980, 147-148.
Chvapil, "Collagen Sponge: Theory and Practice of Medical Applications," J. Biomed. Mater. Res., 1977, 721-741, 11.
Clark et al., "The Influence of Triamcinolone Acetonide on Joint Stiffness in the Rat," The Journal of Bone and Joint Surgery, 1971, 1409-1414, 53A (7).
Cohen et al., "Organization and Adhesive Properties of the Hyaluronan Pericellular Coat of Chondrocytes and Epithelial Cells," Biophysical Journal, 2003, 1996-2005, 85.
Cui et al., "The Comparison of Physicochemical Properties of Four Cross-linked Sodium Hyaluronate Gels With Different Cross-linking Agents," Advanced Materials Research, 2012, 1506-1512, 396-398.
Decision from the Opposition Division for European Patent No. EP-B-2 289 945, dated Jun. 30, 2017.
Decision T1250/10-3.3.03 de la Chambre de Recourse 3.3.03 dated Nov. 5, 2012.
Declaration of Dr. Sebastien Pierre to the EPO in the matter of European Patent: 2289945, Proprietor: Allergan Industrie, dated Jul. 7, 2016.
Deland, "Intrathecal Toxicity Studies with Benzyl Alcohol," Toxicology and Applied Pharmacology, 1973, 153-6, 25, Academic Press, Inc.
Desai et al., "Molecular Weight of Heparin Using 13C Nuclear Magnetic Resonance Spectroscopy," J Pharm Sci., 1995, 212-5, 84 (2).
EP 2289945 Counterstatements, Dec. 21, 2015, EP.
EP 2289945 Notification of Opposition, Dec. 16, 2015, EP.
European Pharmacopoeia 5th Ed., Main vol. 5.0, 2005 with Supplements 5.1 and 5.2, Sodium Hyaluronate.
Eyre et al., "Collagen Cross-Links," Top Curr Chem, 2005, 207-229, 247, Springer-Verlag, Berlin Heidelberg.
Falcone et al., "Crosslinked Hyaluronic Acid Dermal Fillers: A Comparison of Rheological Properties," Journal of Biomedical Materials Research, 2008, 264-271, 87 (1).
Falcone et al., "Temporary Polysaccharide Dermal Fillers: A Model for Persistence Based on Physical Properties", Dermatologic Surgery, 2009, 1238-1243, 35 (8).
Farley et al., "Diluting Lidocaine and Mepivacaine in Balanced Salt Solution Reduces the Pain of Intradermal Injection," Regional Anesthesia, 1994, 48-51, 19 (1).
Frati et al., "Degradation of Hyaluronic Acid by Photosensitized Riboflavin In Vitro. Modulation of the Effect by Transition Metals, Radical Quenchers, and Metal Chelators," Free Radical Biology Medicine, 1996, 1139-1144, 22 (7).
Fujinaga et al., "Reproductive and Teratogenic Effects of Lidocaine in Sprague-Dawley Rats," Anesthesiology, 1986, 626-632, 65.
Gammaitoni et al., "Pharmacokinetics and Safety of Continuously Applied Lidocaine Patches 5%," Am J Health Syst Pharm, 2002, 2215-2220, 59.
Ginshicel Mh, Hydroxy Propyl Methyl Cellulose, Retrieved on Nov. 12, 2008 http://www.ginshicel.cn/MHPC.html, 2007, p. 1-3, 2 (3).
Gold, "Use of Hyaluronic Acid Fillers for the Treatment of the Aging Face," Clin. Interventions Aging, 2007, 369-376, 2 (3).
Goldberg, "Breakthroughs in US dermal fillers for facial soft-tissue augmentation," Journal of Cosmetic and Laser Therapy, 2009, 240-247, 11, Informa UK Ltd.
Gomis et al., "Effects of Different Molecular Weight Elastoviscous Hyaluronan Solutions on Articular Nociceptive Afferents," Arthritis and Rheumatism, Jan. 2004, 314-326, 50(1).
Graefe et al., "Sensitive and Specific Photometric Determination of Mannitol," Clin Chem Lab Med, 2003, 1049-1055, 41 (8).
Grecomoro et al., "Intra-articular treatment with sodium hyaluronate in gonarthrosis: a controlled clinical trial versus placebo," Pharmatherapeutica, 1987, 137-141, 5 (2).
Grillo et al., "Thermal Reconstitution of Collagen From Solution and the Response to Its Heterologous Implantation," JSR, 1962, 69-82, 2 (1).
Harding et al., "Molecular Weight Determination of Polysaccharides," Advances in Carbohydrate Analysis, 1991, 63-144, vol. 1, JAI Press Ltd.
Hassan et al., "Effects of Adjuvants to Local Anaesthetics on Their Duration. III. Experimental Studies of Hyaluronic Acid," Acta Anaesthesiol Scand., 1985, 1, 29 (4).
Hayashibara, "AA2G," Sep. 23, 2007, Retrieved on Jan. 17, 2012, http://web.archive.org/web/20070923072010/http://www.hayashibara-intl.com-/cosmetics/aa2g.html.
Helliwell, "Use of an objective measure of articular stiffness to record changes in finger joints after intra-articular injection of corticosteroid," Annals of Rheumatic Diseases, 1997, 71-73, 56.
Hertzberger-Ten et al., "Intra-articular steroids in pauciarticular juvenile chronic arthritis, type 1," European Journal of Pediatrics, 1991, 170-172, 150.
Hetherington et al., "Potential for Patient Harm from Intrathecal Administration of Preserved Solutions," Med J Aust., 2000, 1, 173(3).
Hurst, "Adhesive Arachnoiditis and Vascular Blockage Caused by Detergents and Other Chemical Irritants: An Experimental Study," J Path. Bact., 1955, 167, 70.
Intramed (PTY) Ltd, Intramed Mannitol 20% m/v Infusion, Package Insert, Jan. 1979, 4 pp. 12-214/8-94, ZA.
Jones et al., "Intra-articular hyaluronic acid compared to intra-articular triamcinolone hexacetonide in inflammatory knee osteoarthritis," Osteoarthritis and Cartilage, 1995, 269-273, 3.
Juvederm Volux, Product Insert, Jul. 26, 2018, 65 pages.
Kablik et al., "Comparative Physical Properties of Hyaluronic Acid Dermal Fillers," Dermatology Surgery, 2009, 302-312, 35.
Kasten, "Volumisierung des Mittelgesichts," Apr. 2014, retrieved from http://www.zwp-online.info/archiv/pub/sim/fa/2014/fa0414/fa0414_10_14_kasten.pdf, 5 pages.
Klein, "Skin Filling Collagen and Other Injectables of the Skin," Fundamentals of Cosmetic Surgery, 2001, 491-508, 3 (19).
Kogan et al., "Hyaluronic Acid: A Biopolymer with Versatile Physico-Chemical and Biological Properties," Handbook of Polymer Research: Monomers, Oligomers, Polymers and Composites, 2007, 415-416, Chapter 31, Nova Science Publishers, Inc.
Kopp et al., "The Short-term Effect of Intra-articular Injections of Sodium Hyaluronate and Corticosteroid on Temporomandibular Joint Pain and Dysfunction," Journal of Oral and Maxillofacial Surgery, 1985, 429-435, 43.
Kulicke et al., "Visco-Elastic Properties of Sodium Hyaluronate Solutions," Institute for Technical and Macromolecular Chemistry, 2008, 585-587, DE.
Laeschke, "Biocompatibility of Microparticles Into Soft Tissue Fillers," Semin Cutan Med Surg, 2004, 214-217, 23.

(56) References Cited

OTHER PUBLICATIONS

Lamar et al., "Antifibrosis Effect of Novel Gels in Anterior Ciliary Sclerotomy (ACS)," 2002, 1 Page, The Association for Research in Vision and Ophthalmology, Inc.
Levy et al., "Lidocaine Hypersensitivity After Subconjunctival Injection", Can J Ophthalmol, 2006, 204-206, 41.
Lindvall et al., "Influence of Various Compounds on the Degradation of Hyaluronic Acid by a Myeloperoxidase System", Chemico-Biological Interactions, 1994, 1-12, 90.
Lupo, "Hyaluronic Acid Fillers in Facial Rejuvenation," Seminars in Cutaneous Medicine and Surgery, 2006, 122-126, 25.
Mackley et al., "Delayed-Type Hypersensitivity to Lidocaine," Arch Dermatol, 2003, 343-346, 139.
Mancinelli et al., "Intramuscular High-dose Triamcinolone Acetonide in the Treatment of Severe Chronic Asthma," West J Med, 1997, 322-329, 167 (5).
Matsumoto et al., "Reducing the Discomfort of Lidocaine Administration Through pH Buffering," Journal of Vascular and Interventional Radiology, 1994, 171-175, 5 (1).
McCarty et al., "Inflammatory Reaction after Intrasynovial Injection of Microcrystalline Adrenocorticosteroid Esters," Arthritis and Rheumatism, 1964, 359-367, 7 (4).
McCleland et al., "Evaluation of Artecoll Polymethylmethacrylate Implant for Soft-Tissue Augmentation: Biocompatibility and Chemical Characterization," Plastic & Reconstructive Surgery, 1997, 1466-1474, 100 (6).
McPherson et al., "Development and Biochemical Characterization of Injectable Collagen," Journal of Dermatol Surg Oncol, 1988, 13-20, 14 (Suppl 1) 7.
Millay et al., "Vasoconstrictors in Facial Plastic Surgery," Arch Otolaryngol Head Neck Surg., 1991, 160-163, 117.
News Release, Mandom Corporation, May 31, 2010, 9 pages including English language translation.
Orvisky et al., "High-molecular-weight Hyaluronan—a Valuable Tool in Testing the Antioxidative Activity of Amphiphilic Drugs Stobadine and Vinpocetine," Journal of Pharm. Biomed. Anal., 1997, 419-424, 16.
Osmitrol (generic name Mannitol), Official FDA Information, side effects and uses, http://www.drugs.com/pro/osmitrol.html, 2010, 10 Pages.
Park et al., "Biological Characterization of EDC-Crosslinked Collagen-Hyaluronic Acid Matrix in Dermal Tissue Restoration," Biomaterials, 2003, 1631-1641, 24.
Park et al., "Characterization of Porous Collagen/Hyaluronic Acid Scaffold Modified by 1-Ethyl-3-(3-Dimethylaminopropyl)Carbodiimide Cross-Linking," Biomaterials, 2002, 1205-1212, 23.
Pierre, et al., "Basics of Dermal Filler Rheology," Dermatol Surg, 2015, vol. 41, pp. S120-S126.
Powell, "Stability of Lidocaine in Aqueous Solution: Effect of Temperature, pH, Buffer, and Metal Ions on Amide Hydrolysis," Pharmaceutical Research, 1987, 42-45, 4 (1).
Prestwich, "Evaluating Drug Efficacy and Toxicology in Three Dimensions: Using Synthetic Extracellular Matrices in Drug Discovery," Accounts of Chemical Research, Jan. 2008, 139-148, 41(1).
Ramos-E-Silva et al., "Stylage: a range of hyaluronic acid dermal fillers containing mannitol. Physical properties and review of the literature," 2013, Clinical, Cosmetic and Investigational Dermatology, pp. 257-261.
Rehakova et al., "Properties of Collagen and Hyaluronic Acid Composite Materials and Their Modification by Chemical Crosslinking," Journal of Biomedical Materials Research, 1996, 369-372, 30, US.
Remington's Pharmaceutical Sciences, 1980, 16th Edition, Mack Publishing Company, Easton, Pennsylvania.
Response to Summons to attend Oral Proceedings under Rule 115(1) EPC of Nov. 10, 2016, Opposition against EP 2289945 Proprietor: Allergan Idustrie Opponent: Merz Pharma GmbH & Co. KGaA, Dated Apr. 26, 2017.
Restyane Silk—Summary of Safety and Effectiveness Data, PMA No. P040024/s72, Jun. 2014, retrieved from https://www.accessdata.fda.gov/cdrh_docs/pdf4/P040024S072b.pdf, 33 pages.
Rosenblatt et al., "The Effect of Collagen Fiber Size Distribution on the Release Rate of Proteins From Collagen Matrices by Diffusion," J Controlled Release, 1989, 195-203, 9.
Rosenblatt et al., "Chain Rigidity and Diffusional Release in Biopolymer Gels," Controlled Release Society, 1993, 264-265, 20.
Sannino et al., "Crosslinking of Cellulose Derivatives and Hyaluronic Acid With Water-Soluble Carbodiimide," Polymer, 2005, 11206-11212, 46.
Schilling et al., Is Human Height Bimodal, The American Statistician, 2002, 223-229, 56 (3), US.
Sculptra® (injectable poly-L-lactic acid) Directions for Use, Product Insert, Jul. 2004, 12 Pages, Dermik Laboratories.
Segura et al., "Crosslinked Hyaluronic Acid Hydrogels: A Strategy to Functionalize and Pattern," Biomaterials, 2005, 359-371, 26 (4).
Selvi et al., "Arthritis Induced by Corticosteroid Crystals," The Journal of Rheumatology, 2004, 622, 31 (3).
Serban et al., "Modular Extracellular Matrices: Solutions for the Puzzle," Methods, 2008, 93-98, 45 (1).
Shu et al., "Synthesis and evaluation of injectable, in situ crosslinkable synthetic extracellular matrices for tissue engineering," Journal of Biomedical Materials Research, 2006, 902-912, 79A.
Silver et al., "Physical Properties of Hyaluronic Acid and Hydroxypropylmethylcellulose in Solution: Evaluation of Coating Ability," Journal of Applied Biomaterials, 1994, 89-98, 5.
Skardal et al., "Bioprinting Vessel-Like Constructs Using Hyaluronan Hydrogels Crosslinked With Tetrahedral Polyethylene Glycol Tetracrylates," Biomaterials, 2010, 6173-6181, 31.
Smith et al., "Five Percent Lidocaine Cream Applied Simultaneously to the Skin and Mucosa of the Lips Creates Excellent Anesthesia for Filler Injections," Dermatol Surg, 2005, 1635-1637, 31.
Tezel et al., "The science of hyaluronic acid dermal fillers," Journal of Cosmetic and Laser Therapy, 2008, 35-42, 10.
The European Aesthetic Guide, Spring 2011, Dermal Filler Comparison Chart, pp. 89-99.
"Varioderm es," Dec. 2011, retrieved from http://www.circugiadeavanzada.com/pdf/varioderm/pdf, 16 pages.
Visiol, TRB Chemedica Ophthalmic Line, Product Info, May 2014, p. 1-2, Geneva, CH.
Visiol, Viscoelstic Gel for Use in Ocular Surgery, http://www.trbchemedica.com/index.php/option=com_content&tas, 2010, 1 Page.
Wagner, "The Mark-Houwink-Sakurada Equation for the Viscosity of Linear Polyethylene," J. Phys. Chem. Ref. Data, 1985, 611-617, vol. 14, No. 2.
Wahl, "European Evaluation of a New Hyaluronic Acid Filler Incorporating Lidocaine," Journal of Cosmetic Dermatology, 2008, 298-303, 7.
Waraszkiewicz et al., "Stability-Indicating High-Performance Liquid Chromatographic Analysis of Lidocaine Hydrochloride and Lidocaine Hydrochloride with Epinephrine Injectable Solutions," Journal of Pharmaceutical Sciences, 1981, 1215-1218, 70 (11).
Weidmann, "New Hyaluronic Acid Filler for Subdermal and Long-lasting Volume Restoration of the Face," European Dermatology, 2009, 65-68.
Weidmann, "Varioderm—eine Innovation im Bereich der Hyaluronsauren," Jun. 2007.
Xia et al., "Comparison of Effects of Lidocaine Hydrochloride, Buffered Lidocaine, Diphenhydramine, and Normal Saline After Intradermal Injection," Journal of Clinical Anesthesia, 2002, 339-343, 14.
Yeom et al., "Effect of Cross-Linking Reagents for Hyaluronic Acid Hydrogel Dermal Fillers on Tissue Augmentation and Regeneration," Bioconjugate Chemistry, 2010, 240-247, 21, American Chemical Society.
Yui et al., "Inflammation Responsive Degradation of Crosslinked Hyaluronic Acid Gels," Journal of Controlled Release, 1992, 105-116, 26.

(56) References Cited

OTHER PUBLICATIONS

Yui et al., "Photo-Responsive Degradation of Heterogeneous Hydrogels Comprising Crosslinked Hyaluronic Acid and Lipid Microspheres for Temporal Drug Delivery," Journal of Controlled Release, 1993, 141-145, 26.

Yun et al., "Hyaluronan Microspheres for Sustained Gene Delivery and Site-Specific Targeting," Biomaterials, 2004, 147-157, 25, US.

Zheng et al., "In Situ Crosslinkable Hyaluronan Hydrogels for Tissue Engineering," Biomaterials, 2004, 1339-1348, 25.

Zulian et al., "Triamcinolone Acetonide and Hexacetonide Intra-Articular Treatment of Symmetrical Joints in Juvenile Idiopathic Arthritis: A Double-Blind Trial," Rheumatology, 2004, 1288-1291, 43.

EP 16704566.5 3rd Party Observations, dated Sep. 4, 2020, 30 pages.

"Mark-Houwink-Gleichung," from https://de.wikipedia.org/wiki/Mark-Houwink-Gleichung, Dec. 2017, 3 pages including English language translation.

"Molmassenverteilung," from https://de.wikipedia.org/wiki/Molmassenverteilung, Dec. 2017, 9 pages including English language translation.

Carruthers et al., "Volumizing with a 20-mg/ml Smooth, Highly Cohesive, Viscous Hyaluronic Acid Filler and its Role in Facial Rejuvenation Therapy," Dermatologic Surgery, 2010, vol. 36, pp. 1886-1892.

"Molecular Weight," The University of Southern Mississippi, 2005, 5 pages.

Math Review, Educational Testing Service, 2017, from https://ets.org/s/gre/pdf/gre_math_review.pdf, 198 pages.

Wikipedia page on "Educational Testing Service," from https://en.wikipedia.org/wiki/Educational_Testing_Service, last edited Nov. 2020.

Stanford Chemicals Company, Certificate of Analysis, Sodium Hyaluronate. Analysis Date Jan. 15, 2015, Retest date Jan. 10, 2017. Web. Aug. 13, 2023. 1 page.

* cited by examiner

COMPOSITIONS AND METHODS FOR IMPROVING SKIN APPEARANCE

CROSS-REFERENCE TO RELATED APPLICATIONS

This application is a continuation of U.S. Application Ser. No. 16/877,315, filed May 18, 2020, issued as U.S. Pat. No. 11,260,015, which is a divisional of U.S. Application Ser. No. 15/549,990, filed Aug. 9, 2017, abandoned, which is a U.S. National Phase Application under 37 C.F.R. § 371 based upon International Application No. PCT/EP2016/052682, filed Feb. 9, 2016, which claims the benefit of and priority to International Application No. PCT/IB2015/000347, filed Feb. 9, 2015, the entireties of each of which is incorporated herein by reference.

FIELD OF THE INVENTION

The present invention generally relates to injectable compositions and more specifically relates to hyaluronic acid-based compositions for treatment of fine lines in skin.

Current injectable treatment options for improving skin quality over the full-face or other significant surface area of skin require multiple treatment sessions (typically 3-4 treatments, every three to four weeks) and have a relatively short duration of effect.

Skin is composed of the epidermis and the dermis. The outermost epidermis is made up of stratified squamous epithelium with an underlying basement membrane. It contains no blood vessels, and is nourished by diffusion from the dermis. The main type of cells which make up the epidermis are keratinocytes, with melanocytes and langerhans cells being also present. This layer of skin is responsible for keeping water in the body and keeping harmful chemicals and pathogens out.

The dermis lies below the epidermis and contains a number of structures including blood vessels, nerves, hair follicles, smooth muscle, glands and lymphatic tissue. The dermis (or corium) is typically 3-5 mm thick and is the major component of human skin. It is composed of a network of connective tissue, predominantly collagen fibrils providing support and elastic tissue providing flexibility. The main cell types are fibroblasts, adipocytes (fat storage) and macrophages. Hyaluronic acid (HA) is a part of the dermis composition and is a major component of the extra cellular matrix.

Facial aging occurs as the result of several factors: inherent changes within the skin, effects of gravity, facial muscles acting on the skin (dynamic lines), soft tissue loss or shift and bone loss and loss of tissue elasticity. The skin ages when the epidermis begins to thin, causing the junction with the dermis to flatten. Collagen decreases as a person ages and the bundles of collagen, which gives the skin turgor, become looser and lose strength. When the skin loses elasticity, it is less able to resist stretching. Coupled with gravity, muscle pull and tissue changes, the skin begin to wrinkle. Water loss and breakdown of bonds between cells also reduces the barrier function of the skin, which can cause the skin's pore size to increases.

It is well known that the eyes are often the first facial feature to show signs of aging. Skin changes around the eyes occur earlier than in the rest of the face since the skin is thinner around the eyes. The skin here contains fewer glands and is subjected to constant blinking, squinting, rubbing, and pulling. The midface ages when the cheeks begin to droop, causing nasolabial folds. Nasolabial folds are the lines that run from the sides of the nose to the corners of the mouth. In the lower face area, as the face ages, facial tissues descend. This results in the so-called "laugh lines". These and other folds and wrinkles are now commonly treated with subdermal and dermal injections of aesthetic facial fillers which add lost volume to the skin thereby reducing the appearance of the folds and wrinkles.

Hyaluronic acid (HA), also known as hyaluronan, is now one of the most commonly used components of dermal fillers. Hyaluronic acid is a naturally occurring, water soluble polysaccharide, specifically a glycosaminoglycan, which is a major component of the extra-cellular matrix and is widely distributed in animal tissues. The identical structure of hyaluronic acid in all species and tissues makes this polysaccharide an ideal substance for use as a bio-material in health and medicine.

HA has excellent biocompatibility and, unlike collagen, does not require any skin testing before implantation. In addition, HA has the ability to bind to large amounts of water, making it an excellent volumizer of soft tissues.

To enhance its longevity in vivo, the HA in dermal fillers is commonly crosslinked. Chemically crosslinked HA is formed by reacting uncrosslinked HA with a crosslinking agent under suitable reaction conditions.

It is generally accepted that HA-based dermal fillers having a high viscosity, for example, those that are highly crosslinked and/or made of high molecular weight HA and/or having a high HA concentration tend to last longer in the body. Conversely, it is generally accepted that HA-based dermal fillers having a low viscosity, for example, those that are more lightly crosslinked and/or made up of low molecular weight HA and/or have a low HA concentration, may have a shorter duration in the body. Naturally, injection of a high viscosity material through a needle is relatively more difficult, and generally requires a lower gauge needle (for instance, 21 G or 23 G compared to 27 G or 30 G) than injection of a relatively low viscosity material. It has proven difficult to develop an HA based composition that is both easy to inject through a high gauge needle (i.e. thin needle) and which has extended duration in the body.

SUMMARY

The present invention relates to injectable compositions, and more specifically, to injectable compositions for intradermal injection into skin. The compositions and methods provide improved skin appearance and quality by filling of superficial skin depressions, and/or improving skin quality and appearance. In one aspect, the compositions and methods provide at least one of improved skin texture, increased skin hydration and increased elasticity.

In one aspect, the present compositions are based on hyaluronic acid (HA) and pharmaceutically acceptable salts of HA, for example, sodium hyaluronate (NaHA). Many of the long lasting, highly injectable compositions of the present invention include a crosslinked HA matrix made with relatively low molecular weight HA. In some embodiments, the compositions have a relatively low concentration of HA. Advantageously, many of the compositions provided herein have an extended duration of effect. For example, rather than requiring multiple repeated treatments every three to four weeks, as is common with conventional intradermal injection treatment methods, many of the present compositions and methods provided herein have a duration of effect of three months, four months, six months, to a year or more.

In a broad aspect of the invention, a composition is provided which generally comprises an HA gel containing, or consisting essentially of, a low molecular weight HA material. The HA component includes more than 50%, for example, at least 70%, for example, about 90% by weight of the low molecular weight HA. The low molecular weight HA material has a weight average molecular weight of no greater than about 0.20 MDa and about 0.99 MDa such as about 0.4 MDa to about 0.8 MDa.

In some embodiments, the HA gel may further contain a high molecular weight HA, that is, a HA material having a molecular weight of at least about 1.0 MDa to about 4.0 MDa. Generally, in embodiments of the invention including high molecular weight HA material, the weight average molecular weight of the high molecular weight HA material is at least twice that of the low molecular weight HA material.

The HA of the HA gel may be crosslinked. For example, the HA may be chemically crosslinked by a suitable crosslinking agent. In some embodiments, the crosslinking agent is selected from the group consisting of 1,4-butanediol diglycidyl ether (BDDE), or 1,4-bis(2,3-epoxypropoxy)butane, or 1,4-bisglycidyloxybutane (all of which are commonly known as BDDE), 1,2-bis(2,3-epoxypropoxy)ethylene and 1-(2,3-epoxypropyl)-2,3-epoxycyclohexane.

In some embodiments, the composition has an HA concentration of about 10.0 mg/g up to about 17.0 mg/g. In some embodiments, the HA concentration is less than about 17.0 mg/g, for example, less than about 15.0 mg/g. In some embodiments, the HA concentration is between about 10.0 mg/g and about 14.0 mg/g. In some embodiments, the HA concentration is about 10.0 mg/g, about 11.0 mg/g, about 12.0 mg/g, about 13.0 mg/g, or about 14.0 mg/g.

In another aspect of the invention, methods of treating skin using the present compositions are provided. For example, methods of improving one or more qualities of skin, or improving appearance or texture of skin, are provided.

In one aspect, methods of treating dryness, texture or roughness, and/or elasticity in skin are provided. The methods generally comprise treating an area of skin by introducing, into the area, multiple, spaced apart injections of a composition comprising a hyaluronic acid (HA) gel containing crosslinked HA, wherein the treated skin maintains an improved hydration, smoother texture or increased elasticity, due to the treatment for an extended duration, for example, for at least about 3 months to about a year or more. In a particularly advantageous embodiment, the step of introducing is performed in only a single treatment session, thereby eliminating the need for repeated treatments to maintain the duration of effect.

In some embodiments, the step of introducing comprises introducing the composition in injections spaced apart by a distance of between about 2 mm to about 30 mm. For example, the step of introducing comprises introducing the composition in injections spaced apart by a distance of between about 5 mm to about 20 mm, or about 10 mm to about 15 mm. In some embodiments, the compositions are introduced at an injection depth of between about 500 microns and about 2000 microns, for example, a depth of about 1000 microns. In preferred embodiments, the compositions are introduced at an injection depth of between about 0.5 mm to about 5.0 mm, preferably about 1.0 mm to about 4.0 mm, more preferably from about 1.5 mm to about 3.0 mm. In general, a deeper injection provides improved hydration results.

In another aspect, the invention provides a method of treating roughness in skin comprising treating an area of skin by introducing, into the area, multiple, spaced apart injections of a composition comprising a hyaluronic acid (HA) gel containing crosslinked HA, wherein the treated skin maintains a smoother texture due to the treatment for at least about 3 months, at least about 4 months, at least about 6 months, or at least about 12 months.

DETAILED DESCRIPTION

Figure 1:
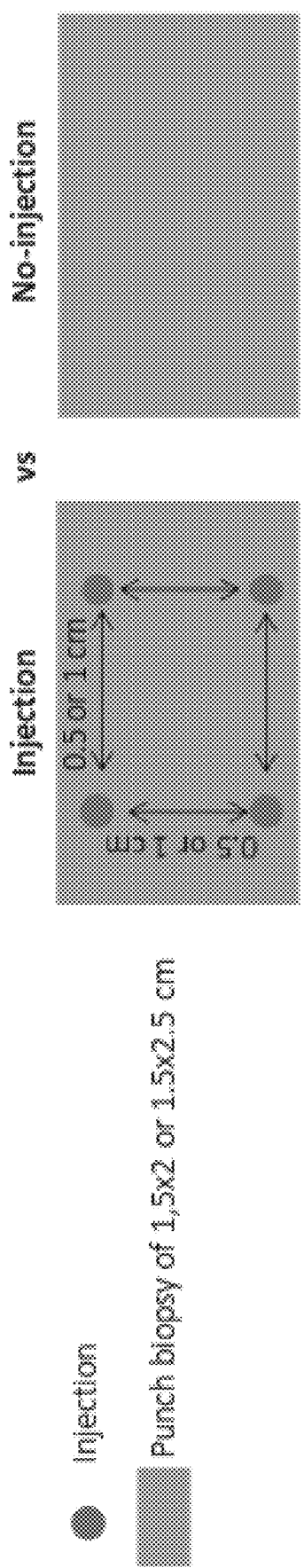
FIG. 1 illustrates the method of injection on the punch biopsy. The explants used for corneometry were treated with 4×10 µl of the injectable composition (square injection) with each point of injection separated by 0.5 cm. The explants of the batch C2 used for corneometry were treated with 4×10 µl of the injectable product (square injection) with each point of injection separated by 1 cm. The untreated controls (T) did not receive any treatment.

The term "about" in the context of numerical values will be readily understood by a person skilled in the art, and preferably means that specific values may be modified by +/−10%. As regards endpoints of ranges, the modifier "about" preferably means that the lower endpoint may be reduced by 10% and the upper endpoint increased by 10%. It is also contemplated that each numerical value or range disclosed in this application can be absolute, i.e. that the modifier "about" can be deleted.

All numbers herein expressing "molecular weight" of HA are to be understood as indicating the weight average molecular weight (Mw) in Daltons.

The molecular weight of HA is calculated from an intrinsic viscosity measurement using the following Mark Houwink relation:

$$\text{Intrinsic Viscosity}(m^3/kg) = 9.78 \times 10^{-5} \times Mw^{0.690}$$

The intrinsic viscosity is measured according to the procedure defined European Pharmacopoeia (HA monograph N°1472, January 2009).

High molecular weight HA as used herein describes a HA material having a molecular weight of at least about 1.0 million Daltons (Mw≥106 Da or 1 MDa) to about 5.0 MDa. For example, the high molecular weight HA in the present compositions may have a molecular weight in the range about 1.5 MDa to about 3.0 MDa, or the high molecular weight HA may have a weight average molecular weight of about 2.0 MDa. In another example, the high molecular weight HA may have a molecular weight of about 3.0 MDa. In another example, the high molecular weight HA may have a molecular weight of about 1 MDa which corresponds to an intrinsic viscosity of 1.35 m3/kg when calculated according to the Mark Houwink relation as indicated above, 1.5 MDa (1.35 m3/kg), 2 MDa (2.18 m3/kg), 3 MDa (2.88 m3/kg), 5 MDa (4.10 m3/kg), 0.2 MDa (0.44 m3/kg), 0.4 MDa (0.72 m3/kg), 0.8 MDa (1.1 m3/kg), 0.99 MDa (1.34 m3/kg).

Low molecular weight HA as used herein describes a HA material having a molecular weight of less than about 1.0 MDa. Low molecular weight HA can have a molecular weight of between about 200,000 Da (0.2 MDa) to less than 1.0 MDa, for example, between about 400,000 Da and about 800,000 Da, for example about 386,000 Da (0.386 MDa) to about 740,000 Da (0.74 MDa). In some embodiments the low molecular weight HA used to make the crosslinked HA matrix does not exceed 0.99 MDa.

Preferably, the mixture of the low molecular weight HA and high molecular weight HA has a bimodal molecular weight distribution. The mixture may also have a multimodal distribution.

In one aspect of the invention, the compositions comprise HA having a high molecular weight component and a low molecular weight component, and the high molecular weight component has a weight average molecular weight at least twice the weight average molecular weight of the low molecular weight component.

For example, a composition in accordance with this aspect of the invention may include a low molecular weight component having a weight average molecular weight of about 500,000 Da, and a high molecular weight component having a weight average molecular weight of about, or at least about, 1.0 MDa.

In another example, a composition in accordance with the invention may include a low molecular weight component having a weight average molecular weight of about 800,000 Da, and a high molecular weight component having a weight average molecular weight of about, or at least about, 1.6 MDa.

Degree of crosslinking is measured by the final weight ratio of crosslinker to HA disaccharide units.

Uncrosslinked HA as used herein refers to individual HA polymer molecules that are not crosslinked to one another. Uncrosslinked HA generally remains water soluble.

Provided herein are compositions for treating skin, for example, injectable compositions that can be introduced intradermally to improve the appearance or quality of skin, for example, to improve hydration, texture and/or elasticity. The compositions may also be effective for treatment of fine lines in skin and for reducing superficial cutaneous depressions. Methods of making these compositions are also provided, as well as methods of treatment using these compositions. The compositions are based on hyaluronic acids (HA) and pharmaceutically acceptable salts of HA, for example, sodium hyaluronate (NaHA).

As used herein, hyaluronic acid (HA) can refer to any of its hyaluronate salts, and includes, but is not limited to, sodium hyaluronate (NaHA), potassium hyaluronate, magnesium hyaluronate, calcium hyaluronate, and combinations thereof. Both HA and pharmaceutically acceptable salts thereof can be used in this invention.

Generally, the concentration of HA in some of the present compositions is about 10.0 mg/g up to about 17.0 mg/g. In some embodiments, the HA concentration is less than about 17.0 mg/g, for example, less than about 15.0 mg/g. In some embodiments, the HA concentration is between about 10.0 mg/g and about 14.0 mg/g. In some embodiments, the HA concentration is about 10.0 mg/g, about 11.0 mg/g, about 12.0 mg/g, about 13.0 mg/g, or about 14.0 mg/g.

Some of the compositions of the invention include additional agents, for example, anesthetic agents in an amount effective to mitigate pain experienced upon injection of the composition. The anesthetic agent may be selected from the group of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. In one embodiment, at least one anesthetic agent is lidocaine, such as in the form of lidocaine HCl. The compositions described herein may have a lidocaine concentration of between about 0.1% and about 5% by weight of the composition, for example, about 0.2% to about 1.0% by weight of the composition. In one embodiment, the composition has a lidocaine concentration of about 0.3% by weight (w/w %) of the composition.

In some embodiments, the compositions further comprise a beneficial additive, for example, an antioxidant. In some embodiments, the compositions include, for example, mannitol. The mannitol may be present in an amount of between about 0.1% w/w to about 2.0% w/w, or between about 0.3% to about 0.9% w/w. In some embodiments, the mannitol is present in an amount of less than, no greater than, or about 1.0% w/w. In some embodiments, the mannitol is present in an amount of about 0.9% w/w. In other embodiments, the mannitol is present in an amount of about 0.1% w/w, or about 0.2% w/w, or about 0.3% w/w, or about 0.4% w/w, or about 0.5% w/w, or about 0.6% w/w, or about 0.7% w/w, or about 0.8% w/w, or about 0.9% w/w, or about 1.0% w/w. In other embodiments, the mannitol is present in an amount of greater than about 1.0% w/w. In some embodiments, the mannitol is present in an amount of between about 1.0% w/w to about 5.0% w/w.

In some embodiments, the compositions further comprise a vitamin, for example, Vitamin C. In a more preferred embodiment, the vitamin is a derivative or a stabilized form of Vitamin C, for example, ascorbic acid 2-glucoside. The vitamin may be present in an amount of between about 0.1% to about 2.0% w/w, or between about 0.2% and about 1.0% w/w, or between about 0.3% to about 0.6% w/w. In some embodiments, the Vitamin C is present in an amount of about 0.6% w/w. In other embodiments, the Vitamin C derivative is present in an amount of about 0.1% w/w, or about 0.2% w/w, or about 0.3% w/w, or about 0.4% w/w, or about 0.5% w/w, or about 0.6% w/w, or about 0.7% w/w, or about 0.8% w/w, or about 0.9% w/w, or about 1.0% w/w. In other embodiments, the Vitamin C derivative is present in an amount of greater than about 1.0%. In some embodiments, Vitamin C derivative is present in an amount of between about 1.0% w/w to about 5.0% w/w.

In some embodiments, the compositions further comprise a combination of mannitol and ascorbic acid 2-glucoside. In some of these embodiments, the mannitol is present in an amount of no greater than 1.0% w/w, for example, 0.9% w/w and the ascorbic acid 2-glucoside is present in an amount of about 0.6% w/w.

In some embodiments, the compositions do not include an antioxidant or a vitamin. For example, in some embodiments, the compositions comprise or consist essentially of hyaluronic acid crosslinked with a crosslinking agent and water. These compositions may or may not include an anesthetic agent such as lidocaine.

The present products and compositions are preferably provided in a sterile form. The compositions may be sterilized using conventional methods, for example, autoclaving. For example, the compositions may be sterilized by exposing the compositions to temperatures of at least about 120° C. to about 130° C. and/or pressures of at least about 12 pounds per square inch (PSI) to about 20 PSI for a period of at least about 1 minute to about 15 minutes.

Method of making the composition comprise the steps of providing raw HA material in the form of dry HA fibers or powder. The raw HA material may be HA, its salts and/or mixtures thereof. In a preferred embodiment, the HA material comprises fibers or powder of NaHA, for example, bacterial-sourced NaHA fibers. In some aspects of the present description, the HA material may be animal derived. The HA material may be a combination of raw materials including HA and at least one other polysaccharide, for example, glycosaminoglycan (GAG).

In a broad aspect of the invention, the HA material of the compositions may comprise a crosslinked HA matrix made with between about 5% to about 95% low molecular weight HA with the balance of the HA material including high molecular weight HA.

In some embodiments of the invention, the HA material used to make the present compositions nearly entirely comprises or consists of low molecular weight HA. In some embodiments, nearly 100% of the HA material used to make the present compositions may be low molecular weight HA as defined above. In other embodiments, the HA material used to make the compositions comprises a combination of relatively high molecular weight HA and relatively low molecular weight HA, as defined above. In certain embodiments, at least about 50% w/w, for example, at least about 70% w/w, for example, at least about 90% w/w or greater of the HA material in the compositions is a low molecular weight HA as defined above, with the remaining portion of HA being high molecular weight HA. In one embodiment, the compositions are made using a 90:10 ratio of low molecular weight HA to high molecular weight HA. That is, the compositions of these embodiments are made with a combination of high and low molecular weight HA, with about 90% w/w of the HA being the low molecular weight HA.

In one embodiment, the pure, dry NaHA fibers are hydrated in an alkaline solution to produce an uncrosslinked NaHA gel. Any suitable alkaline solution may be used to hydrate the NaHA in this step, for example, but not limited to aqueous solutions containing sodium hydroxide (NaOH), potassium hydroxide (KOH), sodium bicarbonate (NaHCO3), lithium hydroxide (LiOH), and the like. In another embodiment, the suitable alkaline solution is aqueous solutions containing NaOH. The resulting alkaline gel will have a pH above 7.5. The pH of the resulting alkaline gel can have a pH greater than 9, or a pH greater than 10, or a pH greater than 11, or a pH greater than 12, or a pH greater than 13.

The next step in the manufacturing process involves the step of crosslinking the hydrated, alkaline NaHA gel with a suitable crosslinking agent. The crosslinking agent may be any agent known to be suitable for crosslinking polysaccharides and their derivatives via their hydroxyl groups. Suitable crosslinking agents include but are not limited to, 1,4-butanediol diglycidyl ether (or 1,4-bis(2,3-epoxypropoxy)butane or 1,4-bisglycidyloxybutane, all of which are commonly known as BDDE), 1,2-bis(2,3-epoxypropoxy)ethylene and 1-(2,3-epoxypropyl)-2,3-epoxycyclohexane. The use of more than one crosslinking agent or a different crosslinking agent is not excluded from the scope of the present disclosure. In one embodiment, the HA gels described herein are crosslinked using BDDE.

The step of crosslinking may be carried out using any means known to those of ordinary skill in the art. Those skilled in the art appreciate how to optimize conditions of crosslinking according to the nature of the HA, and how to carry out crosslinking to an optimized degree.

In another embodiment, the crosslinking of the HA is accomplished during hydration of the HA fibers, by hydrating the combined high and low molecular weight fibers in an alkaline solution containing a crosslinking agent, for example, BDDE.

The degree of crosslinking in the HA component of the present compositions is at least about 1% and is up to about 20% BDDE/HA, w/w, for example, between about 4% and about 12% w/w, for example, about 10% w/w, for example, about 8% w/w, for example, about 6% w/w, for example, about 5% w/w, for example, about 4% w/w.

The hydrated crosslinked, HA gels may be swollen to obtain the desired HA concentration. This step can be accomplished by neutralizing the crosslinked, hydrated HA gel, for example by adding an aqueous solution containing of an acid, such as HCl. The gels are then swelled in a phosphate buffered saline (PBS) solution.

The gels may be purified by conventional means such as, dialysis against a phosphate buffer, or alcohol precipitation, to recover the crosslinked material, to stabilize the pH of the material and to remove any un-reacted crosslinking agent. The compositions are mixed to achieve homogeneity. Preferably, the homogenization step comprises mixing, stirring, or beating the gels with a controlled shearing force obtaining substantially homogenous mixtures. In some embodiments, during or after the mixing, a phosphate buffer is added to reach the desired concentration of HA in the final composition.

In some embodiments, lidocaine (e.g. in the form of lidocaine HCl), or another suitable anesthetic, is added to the compositions. For example, the pH of the purified, substantially pH neutral, gel is adjusted to cause the gel to become slightly alkaline such that the gels have a pH of greater than about 7.2, for example, about 7.5 to about 8.0. Alternatively, the gel is adjusted to cause the gel to become alkaline such that the gels have a pH of greater than about 9, for example, about 10.0 to about 11.0. This step may be accomplished by any suitable means, for example, by adding to the gels a suitable amount of dilute NaOH, KOH, NaHCO3 or LiOH, or any other alkaline molecule, solution and/or buffering composition know by one skilled in the art. For example, in some embodiments, the lidocaine HCl is provided in a powder form which is solubilized using water for injection (WFI). The lidocaine is then added to the (slightly) alkaline gel. Uncrosslinked HA may then be added to the lidocaine-containing gel, if desired. For example, in one embodiment, the desired HA concentration is about 12.0 mg/g. The compositions including lidocaine may have a lidocaine concentration of between about 0.1% and about 5% by weight of the composition, for example, about 0.3% by weight (or w/w), based on the total weight of the composition. The compositions including uncrosslinked HA may have an uncrosslinked HA concentration of less than 10% w/w or less than 5% w/w such as preferably between about 0.5% and about 1.5% by weight of the composition, for example, about 0.9 to 1.0%, based on the total weight of the composition. The uncrosslinked HA has preferably a high molecular weight.

The compositions are introduced into delivery devices, for example, syringes. Syringes useful according to the present description include any syringe known in the art capable of delivering viscous dermal filler compositions. The syringes may have an internal volume of about 0.4 mL to about 3 mL, between about 0.5 mL and about 1.5 mL or between about 0.8 mL and about 1.0 m L.

In other embodiments, the compositions are introduced into injection devices suitable for delivering the compositions using multiple microdepot injections, into relatively shallow, superficial, surfaces of skin.

The gauges of needles used to deliver the present compositions include gauges of between about 18 G and about 40 G. In some embodiments, the needles for delivering the compositions are between about 25 G to about 33 G such as between about 31 G to about 33 G or about 32 G to about 33 G. In some embodiments, the compositions are delivered using a needle having a gauge of 28 G, 29 G, 30 G, 32 G or 33 G.

In another aspect of the invention, methods of treating skin using the present compositions are provided. For example, methods of improving one or more qualities of skin, or improving appearance or texture of skin, are provided.

In one aspect, methods of treating dryness, texture or roughness, and/or elasticity in skin are provided. The methods generally comprise treating an area of skin by introducing, into the area, multiple, spaced apart injections of a composition comprising a hyaluronic acid (HA) gel containing crosslinked HA, wherein the treated skin maintains an improved hydration, smoother texture or increased elasticity, due to the treatment for an extended duration, for example, for at least about 3 months to about a year or more.

In a particularly advantageous embodiment, the step of introducing is performed in only a single treatment session, thereby eliminating the need for repeated treatments to maintain the duration of effect.

In one aspect of the invention, a method of treating skin in provided comprising introducing the composition into the skin during a treatment session comprising multiple injections of the composition into a skin region.

In one embodiment, a treatment session comprises a single visit by the patient to a practitioner. During the treatment session, multiple injections into the skin, for example into a particular skin region, may be administered.

The multiple injections of a single treatment session may comprise, for example, from 2 to about 500 injections, from about 50 to about 200 injections. In some embodiments, a treatment session comprises, for example, at least 2 injections, at least 10 injections, at least 20 injections, at least 40 injections, at least 60 injections, at least 80 injections, at least 100 injections, at least 140 injections, at least 180 injections, at least 200 injections, at least 300 injections, at least 400 injections at least 500 injections, or more, into the skin region.

In some embodiments, the treatment session takes no longer than about 45 minutes, no longer than about 30 minutes, no longer than about 15 minutes, or no longer than about 10 minutes per treatment area. Treatment area is defined as a skin region being treated with the present compositions and methods. The treatment area may comprise or consist of a skin region of at least one of a face, a neck, or a décolletage. The treatment area may also comprise or consist of a region of skin other than a face, neck or décolletage, for example, a skin region of the top of the hand, a knee, an elbow, a forearm, a calf, a thigh, a back, or any other region of skin that can be treated using the present compositions and methods and can be benefitted or improved thereby.

In some embodiments, the step of introducing comprises introducing the composition in injections spaced apart by a distance of between about 2 mm to about 30 mm. For example, the step of introducing comprises introducing the composition in injections spaced apart by a distance of between about 5 mm to about 20 mm. In some embodiments, the step of introducing comprises introducing the composition in injections spaced apart by a distance of between about 10 mm to about 15 mm.

In some embodiments, the injections are provided at a very superficial depth in the skin. For example, in some embodiments, the compositions are introduced at a depth of no greater than about 2000 microns. For example, the injections may be provided at a depth of about 500 microns to about 2000 microns, about 800 microns to about 1600 microns, about 1000 microns to about 1200 microns. In preferred embodiments, the compositions are introduced at an injection depth of between about 0.5 mm to about 5.0 mm, preferably about 1.0 mm to about 4.0 mm, more preferably from about 1.5 mm to about 3.0 mm. In one embodiment, the injections are introduced in an amount of about 1 µL to about 200 µL, for example, about 5 µL to about 100 µL per injection, for example, between about 20 µL to about 80 µL, for example, about 40 µL to about 60 µL per injection. In some embodiments, the injections are introduced in an amount of about 5 µL to about 500 µL per injection, about 10 µL to about 400 µL, about 50 µL to about 200 µL, or about 100 µL per injection.

In some embodiments, the injections are delivered through a needle having a gauge of at least 27 G, for example, 28 G, 30 G or 32 G.

Advantageously, method of treatment may comprise or consist of a single treatment session lasting a relatively short amount of time. In some embodiments, the treatment session covering the region of skin being treated, comprises multiple, intradermal injections into the skin region, and takes no longer than about 45 minutes. In some embodiments, the treatment session takes no longer than about 30 minutes. In yet other embodiments, the treatment session takes no longer than about 20 minutes, or no longer than about 15 minutes, or no longer than about 10 minutes.

A method of treating roughness in skin is also provided, wherein the method comprises treating an area of skin by introducing, into the area, multiple, spaced apart injections of a composition comprising a hyaluronic acid (HA) gel containing crosslinked HA wherein the treated skin maintains a smoother texture due to the treatment for at least about 3 months, for at least about 4 months, for at least about 6 months, for at least about 9 months, or for at least about 12 months.

In a particular embodiment, the compositions of the invention comprise a sterile physiological solution of hyaluronic acid (HA) gel of non-animal origin cross-linked with 1,4-Butanediol Diglycidyl ether (BDDE) at a concentration of 12 mg/mL. The compositions are useful for treatment of superficial skin depressions as measured by improvement in skin texture and improvement of skin quality, such as smoothness, hydration and elasticity, as compared to non-treated superficial skin depressions. In a particular embodiment, methods of treatment include injections, for example, depot injections, into the dermis using a 32 G needle across the target anatomic region(s). The target anatomic regions include skin regions of the face, and skin regions of the neck. The improvement of skin appearance, for example, reduced appearance of depressions, fine lines and uneven or rough texture as compared to untreated skin, may be markedly noticeable by the patient, and the improvement may last for a duration of at least 4 months, 6 months, 9 months or even 12 months, after a single treatment session lasting only 45 minutes, or only 30 minutes, or only 20 minutes, or only 15 minutes, or less. Improvement of skin texture can be evaluated using appropriate scales. Skin quality measurements of hydration and elasticity can be performed, using appropriate instrumentation, and compared to baseline, i.e. untreated skin. Other evaluation methods, for example, FACE Q and GAIS can be utilized to assess subject and investigator satisfaction, respectively. In a specific embodiment, the duration of action of the product after the treatment is at least about 4 months for example, about 6 months.

The addition of lidocaine to the compositions, in some embodiments, reduces pain in the treatment area. However, in some embodiments, the compositions do not include lidocaine, in order to address patient need with regard to allergy to lidocaine and pain sensitivity.

Another embodiment provides a method of increasing at least one of smoothness, hydration, and elasticity in skin comprising introducing, into a skin region at a depth of between about 500 microns and about 5000 microns, in a single treatment session, multiple, spaced apart injections of a composition comprising a hyaluronic acid (HA) gel containing BDDE-crosslinked HA and uncrosslinked HA, wherein the injections are introduced in an amount of about 5 μL to about 100 μL per injection, wherein the injections are delivered through a needle having a gauge of from 28 G to 33 G, wherein the injections are spaced apart by a distance of between about 5 mm to about 20 mm.

In some embodiments, the skin region maintains an increased smoothness, hydration, and/or elasticity due to the treatment for at least about 3 months, about 4 months, about 5 months, about 6 months, 9 months, 12 months, or longer.

In another embodiment, a composition for increasing at least one of smoothness, hydration, and elasticity in skin is provided comprising a hyaluronic acid (HA) gel comprising a crosslinked HA matrix made with a low molecular weight HA material having a weight average molecular weight of between about 400,000 Da and about 800,000 Da; wherein the HA concentration of the composition is from about 10.0 mg/g to about 14.0 mg/g; and wherein the composition maintains the increased smoothness, hydration, and/or elasticity due to the treatment for at least about 6 months from being introduced into the skin in a single treatment session comprising multiple, spaced apart injections of the composition in which the injections are introduced in an amount of about 5 μL to about 100 μL per injection, delivered through a needle having a gauge of from 28 G to 33 G and are spaced apart by a distance of between about 5 mm to about 20 mm. The skin region may maintain an increased smoothness, hydration, and/or elasticity due to the treatment for at least about 3 months, about 4 months, about 5 months, about 6 months, 9 months, 12 months, or longer. The compositions may further include at least one of a mannitol and a Vitamin C. In some embodiments, both mannitol and a Vitamin C derivative are present in the compositions.

The compositions are associated with a gel hardness G' of between about 50 to 200 Pa, such as 100-150 Pa or 120 Pa, when measured at 0.1 Hz or between about 100 to 300 Pa, such as 150 to 200 Pa or 175 Pa, when measured at 5 Hz. The method for measuring the gel hardness is known in the art. The gel hardness is indicative for the dermal filler's softness.

The compositions are further associated with a gel viscosity G" of between about 10 to 100 Pa, such as 15-40 Pa or 20 Pa, when measured at 0.1 Hz or between about 10 to 100 Pa, such as 20-40 Pa or 30 Pa, when measured at 5 Hz. The method for measuring the viscosity is known in the art.

The compositions are also associated with a compression of between about 5 to 20 N, such as 10-15 N or 12 N. The method for measuring the compression is known in the art. The compression is indicative for the dermal filler's resistance to deformation. Generally, the lower the compression, the lower the filler's lift spreadability, i.e. the filler is then more suitable for treating superficial lines and folds in the face or neck as compared to fillers having a higher compression which are more suitable for deeper injections and volume restorations.

Example 1

The free radical degradation test allows to evaluate the resistance of a gel sample toward the degradation of the HA chains by the free radicals (one of the main degradation pathway of HA). Free radical degradation tests was carried out on 3 different batches of the present compositions. The results obtained are presented on the Table 1. All measures were found to conform (CVr<10%).

TABLE 1

Free radical degradation results for the present compositions

| Gel | | initial viscosity (Pa · s) | degradation time (s) | Conformity |
|---|---|---|---|---|
| LBA2-214 | | 17.7 | 4572 | CF |
| | | 15.5 | 4858 | |
| | | 16.1 | 5044 | |
| | Mean | 16.4 | 4825 | |
| | STD | 1.1 | 238 | |
| | CVr (%) | 7% | 5% | |
| LBA2-263 | | 12.5 | 5377 | CF |
| | | 13.8 | 5009 | |
| | | 13.9 | 4882 | |
| | Mean | 13.4 | 5090 | |
| | STD | 0.8 | 257 | |
| | CVr (%) | 6% | 5% | |
| LBA2-288 | | 13.7 | 5057 | CF |
| | | 14.1 | 5189 | |
| | | 13.7 | 4878 | |
| | Mean | 13.8 | 5041 | |
| | STD | 0.2 | 156 | |
| | CVr (%) | 2% | 3% | |

The inter-batch variability is around 3% on the 3 different batches and the average value of degradation time is 4985 s (Table 2).

TABLE 2

Inter-batch variability for the present compositions degradation times

| | LBA2-214 | LBA2-288 | LBA2-263 |
|---|---|---|---|
| mes1 | 4572 | 5057 | 5377 |
| mes2 | 4858 | 5189 | 5009 |
| mes3 | 5044 | 4878 | 4882 |

TABLE 2-continued

Inter-batch variability for the present compositions degradation times

|  | LBA2-214 | LBA2-288 | LBA2-263 |  |
|---|---|---|---|---|
| mean | 4825 | 5041 | 5089 | 4985 |
| STD | 238 | 156 | 257 | 141 |
| CVr | 5% | 3% | 5% | 3% |

Example 2

A 37-year old woman presents with rough, dry facial skin due to aging, dry climate and/or sun/wind exposure over the course of her lifetime. The physician administers, by intradermal, micro-depot injections, the compositions described herein. The treatment consists of from 10 to about 100 shallow injections per skin region, with a 32 G/4 mm needle. The skin regions treated are the face, neck, and décolleté. The treatment session, over the total of all of the skin regions of the patient, lasts about 40 minutes from the initial injection to the final injection. Each treatment region receives an appropriate amount of the composition in spaced apart injections. The facial region for example, receives about 2 mL to about 3 mL of the composition, administered by shallow single injections spaced apart approximately every 10 mm to about 15 mm. The neck is treated with about 1 mL to 2 mL of the composition, the injections spaced apart approximately every 15 mm to about 20 mm. After the treatment, the areas of the skin treated are examined by the senses of sight, touch and pressure. A photographic evaluation is performed at the beginning and at the end of the treatment. The patient reports to the physician that the treatment has caused only minimum discomfort. The patient returns to her everyday activities immediately after the treatment. In a small area on the skin of her treated right hand, ecchymosis is found, but this resolves a few days after the application of an anti-inflammatory cream. The patient returns to the physician 4 months after the treatment for a follow up evaluation. Prior to the follow up evaluation visit, no further injections of fillers or mesotherapy treatments are performed on the patient. On objective examination at the follow up visit, the treatment has resulted in an improvement in the epidermal texture, and decreased dryness, and improved brightness of the skin. These improvements are evidenced in part by the photographic documentation. The treated skin regions are gently palpated and seem to have an increase in hydration, suppleness, elasticity and tone. The patient expresses a high degree of satisfaction with the treatment via the completion of a self-assessment questionnaire. The patient claims the treated areas have improved and she is very happy with the results. Interestingly, these good results are achieved based on only the single treatment session, with no repeated injections, "top-ups", or further injection treatment between the time of the treatment session and the follow up visit.

Example 3

The hydration of the injectable compositions on the epidermal and dermal structures of human living skin explants has been evaluated by corneometry measurements: Using a CM825 Corneometer® (COURAGE & KHAZAKA) the humidity level of the most external cutaneous layers of the stratum corneum have been determined. The action principle of the Corneometer® is based on the modification of the electrical capacities of the detector which is designed in the form of a condenser. The surface of the measurement head, in contact with the skin, modifies its electrical capacity according to the humidity level of the skin. On D0 (=day 0), the electric epidermal capacitance expressed in AU (arbitrary unit) is an index of the skin hydration. The following composition according to the present disclosure has been determined:

TABLE 3

|  | Composition according to present disclosure (P) |
|---|---|
| NaHA concentration (mg/g) | 10.5-13.5 |
| Lidocaine content (% by weight) | 0.27-0.33 |
| Uncrosslinked HA content having a high molecular weight (% by weight) | 0.95 |

The product has been stored at room temperature within the duration of the study.

Explant preparation: On an abdominal plasty coming from a 45-year-old Caucasian woman, 9 explants were prepared. The explants were kept in survival in BEM medium (BIO-EC's Explants Medium) at 37° C. in a humid, 5%-$CO_2$ atmosphere. The explants were distributed in 3 batches (Nb=Number):

TABLE 4

| Analysis | Batch | Designation | Treatment | Nb and size of explants | Sampling time |
|---|---|---|---|---|---|
| Corneometry | T-C1 | Untreated control (Blank) | / | 3; 1.5 × 2 cm | D 9 |
|  | P-C1 | Product P | Composition according to present disclosure | 3; 1.5 × 2 cm | D 9 |
|  | P-C2 | Product P | Composition according to present disclosure | 3; 1.5 × 2.5 cm | D 9 |

Product application: The explants of the batch C1 used for corneometry were treated with 4×10 µl of the injectable product (square injection) with each point of injection separated by 0.5 cm (see FIG. 1). The explants of the batch C2 used for corneometry were treated with 4×10 µl of the injectable product (square injection) with each point of injection separated by 1 cm (see FIG. 1). The untreated controls did not receive any treatment.

Corneometry: An index of skin hydration, epidermal capacitance, was assessed using the CM825 Corneometer® (COURAGE & KHAZAKA) on the explants at D0, D2, D7 and D9. The measures have been performed at the centre of the square explants using a probe of 1 cm of diameter. Ten measurements are performed and the average value is calculated by the corneometer.

Sampling: On D0, three explants from the batch TO were collected and cut in 2 parts: half was frozen at −80° C. and half was fixed in formol. On D2, D7 and D9, 3 explants from each batch were collected and processed in the same way.

Statistical analysis: The statistical analysis is performed according the Student t-test. Student t test gives the probability "p" for two batches to be significantly different. The difference between two batches is significant if p<0.05(*), so a probability of 95% for two batches to be significantly different; or if p<0.01(**), so a probability of 99% for two batches to be significantly different.

Figure 2:
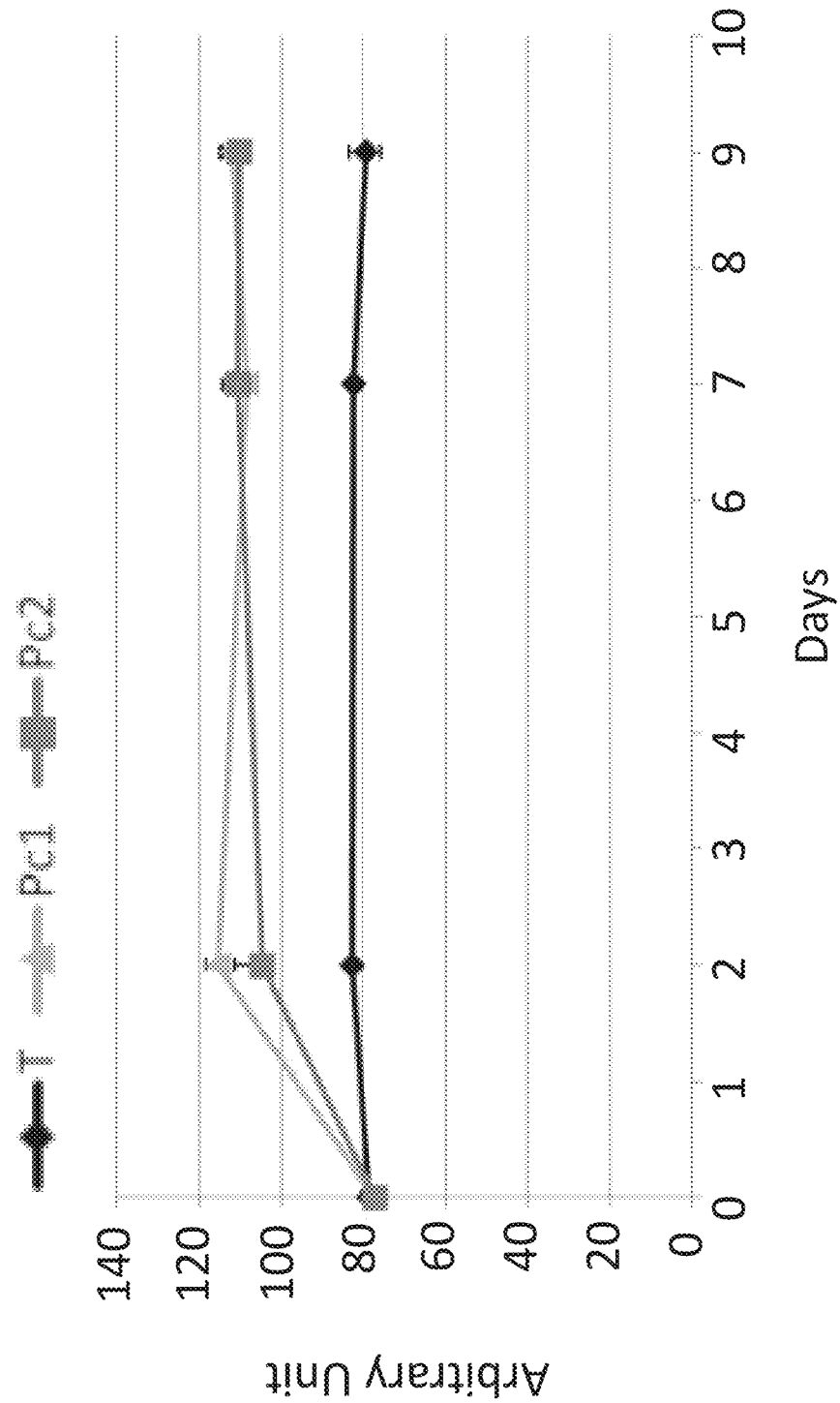
FIG. 2 illustrates corneometry measurements for 3 different human explants, measured at Day 2, Day 7, and Day 9 after injection with placebo (T, diamond), composition P1 (triangle), and composition P2 (square). Data is also shown in Table 5.
Figure 3:
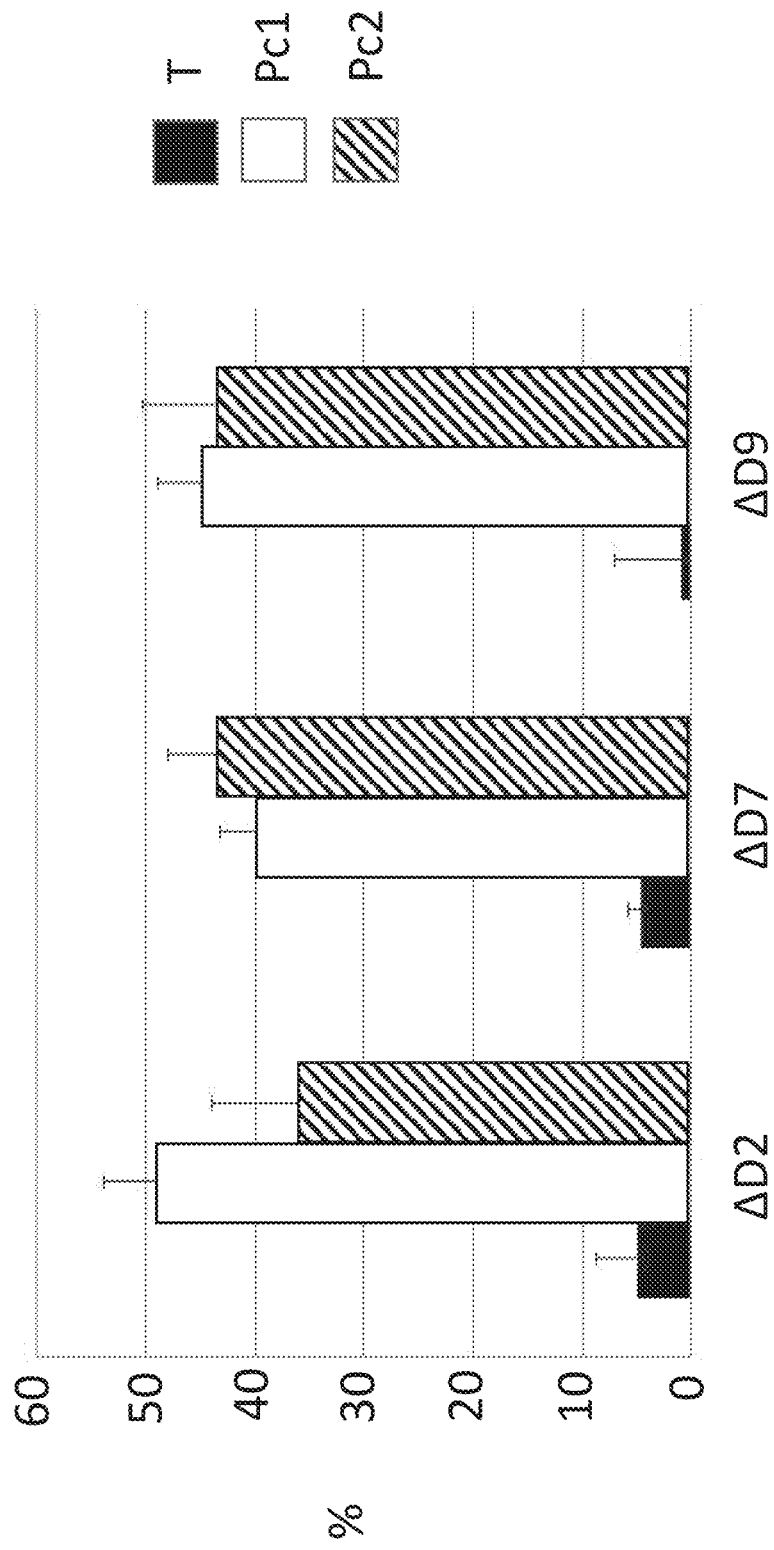
FIG. 3 illustrates percent variation in corneometry values for 3 different human explants, measured at Day 2, Day 7, and Day 9 after injection with placebo (T), composition P1, and composition P2. Data is also shown in Table 5.

RESULTS: Measurement of corneometry for each batch (see also FIGS. 2 and 3):

TABLE 5

| | Corneometry data | | | | | | | |
|---|---|---|---|---|---|---|---|---|
| | D0 | | D2 | | D7 | | D9 | |
| | Average | SD | Average | SD | Average | SD | Average | SD |
| T | 78.9 | 1.7 | 82.7 | 1.3 | 82.5 | 1.0 | 79.5 | 3.9 |
| Pc1 | 77.6 | 1.1 | 115.5 | 2.9 | 108.3 | 2.4 | 112.0 | 2.2 |
| Pc2 | 77.1 | 0.8 | 104.6 | 6.8 | 110.5 | 3.7 | 110.1 | 5.0 |

The corneometry shows that with the product Pc1, the corneometry values are higher by 44.0% vs T on D2, 34.9% vs T on D7, and 43.6%** vs T on D9. With the product Pc2, the corneometry values are higher by 30.7%* vs T on D2, 38.6% vs T on D7, and 41.9% vs T on D9. (According to Student t-test: * significant with p<0.05 (95%); ** significant with p<0.01 (99%)). The compositions according to the present disclosure show a good hydration activity whatever the condition tested (4 injections of 10 µl each separated by 0.5 cm or 1 cm for Pc1 and Pc2 respectively), it induces a strong increment of epidermal capacitance values which increases the skin hydration.

Example 4

The skin hydration of the injectable compositions according to the present disclosure on the epidermal and dermal structures of human living skin explants has been evaluated by additional corneometry measurements. The following compositions have been determined:

TABLE 6

| | Composition including uncrosslinked HA only (P1) | Composition according to present disclosure (P2) |
|---|---|---|
| NaHA concentration (mg/g) | 11.5-15.5 | 10.5-13.5 |
| Lidocaine content | / | 0.27%-0.33% |
| Mannitol content | 0.70%-1.10% | / |
| Uncrosslinked HA content having a high molecular weight (% by weight) | 100% | 0.95% |

The products have been stored at room temperature within the duration of the study.

Explant preparation: For the first donor, 9 explants of 1.5 cm×2 cm in size were prepared on an abdominal plasty coming from a 59-year-old Caucasian woman. For the second donor, 9 explants of 1.5 cm×2 cm in size were prepared on an abdominal plasty coming from a 42-year-old Caucasian woman. For the third donor, 9 explants of 1.5 cm×2 cm in size were prepared on an abdominal plasty coming from a 52-year-old Caucasian woman. For each donor, 9 explants were distributed in 3 batches as follows:

TABLE 7

| Batch | Designation | Treatment | Number of explants | Sampling time |
|---|---|---|---|---|
| T | Untreated Control (Blank) | / | 3 | D 8 |
| P1 | Product 1 | Composition according to present disclosure | 3 | D 8 |
| P2 | Product 2 | Composition including uncrosslinked HA only | 3 | D 8 |

Product application: On D0, 3×50 µL of the products P1 or P2 were injected with a needle into the dermis of the rectangular explants (1.5×2 cm). The untreated controls did not receive any treatment.

Half of the culture medium (1 ml) was refreshed on D1, D2, D5 and D7.

Corneometry: An index of skin hydration, epidermal capacitance, was assessed using the CM825 Corneometer® (COURAGE & KHAZAKA) on the explants at D0, D1, D2 and D8.

Figure 4:
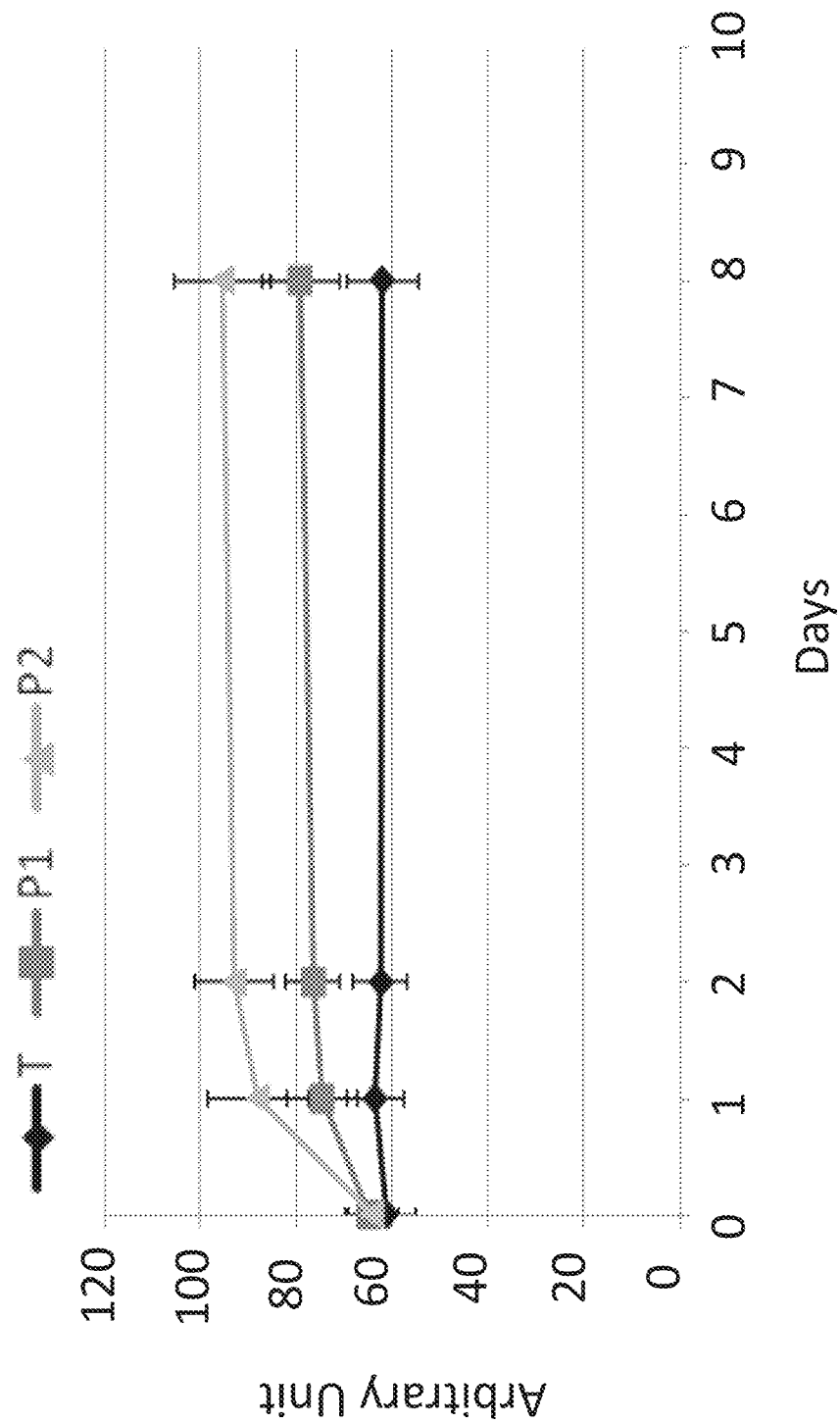
FIG. 4 illustrates corneometry measurements for 3 different human explants, measured at Day 1, Day 2, and Day 8 after injection with placebo (T, diamond), composition P1 (square), and composition P2 (triangle). Data is also shown in Table 8.
Figure 5:
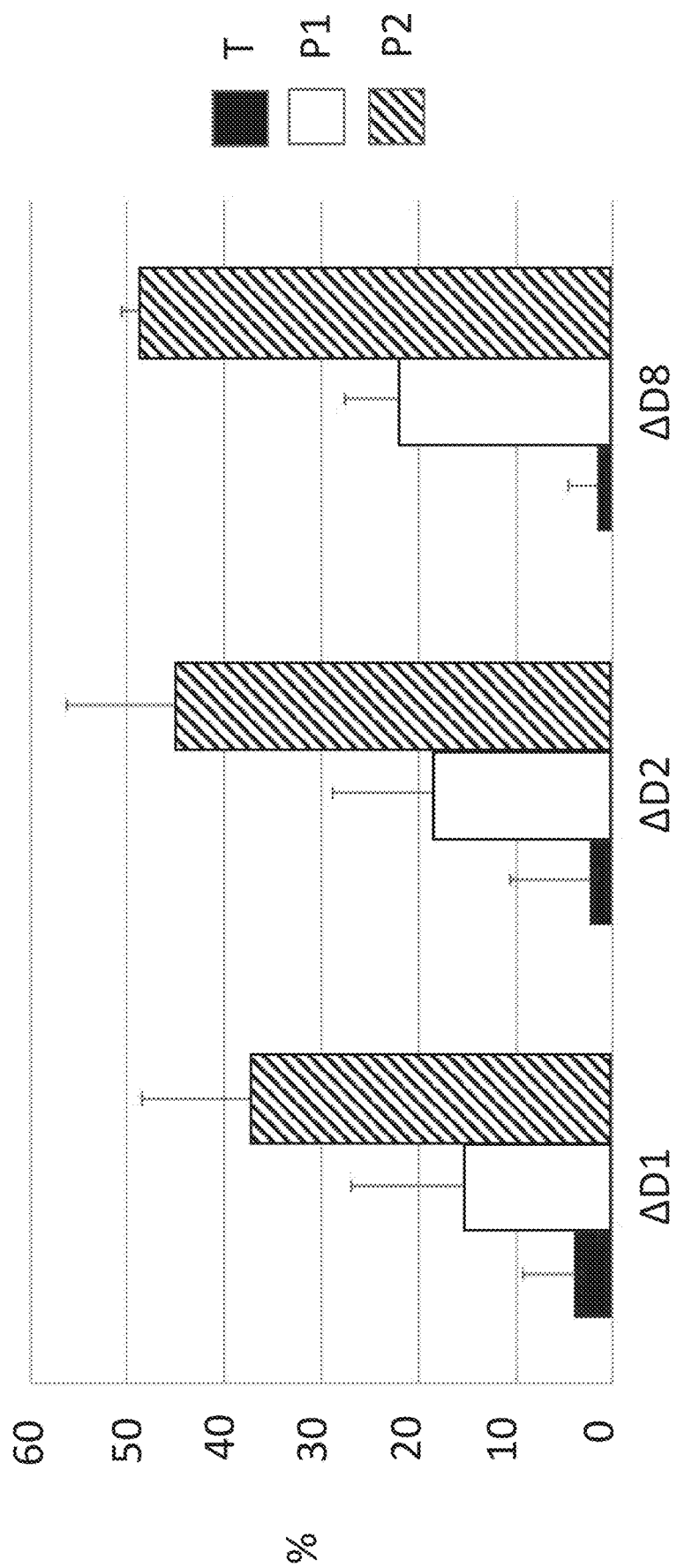
FIG. 5 illustrates variations of corneometry values for 3 different human explants on Day 1, Day 2, and Day 8 after injection with placebo (T), composition P1, and composition P2. Data is also shown in Table 8.

RESULTS: The results of the corneometry measurements for the three donors and expressed as an average of three values (see also FIGS. 4 and 5):

TABLE 8

| | | Day of measurement | | | |
|---|---|---|---|---|---|
| | AU | D 0 | D 1 | D 2 | D 8 |
| Product | T | 61.00 (SD: 5.9) | 63.45 (SD: 6.0) | 62.42 (SD: 5.6) | 61.98 (SD: 7.5) |
| | P1 | 64.76 (SD: 4.3) | 74.64 (SD: 7.3) | 76.54 (SD: 5.6) | 79.03 (SD: 8.2) |
| | P2 | 64.10 (SD: 5.5) | 87.90 (SD: 10.5) | 92.88 (SD: 8.1) | 95.37 (SD: 10.1) |

AU (Arbitrary Units of corneometry)

For the 3 donors, the corneometry shows that the product P1 induces an increase of 15% on D1 of corneometry value compared to D0, continues to increase to 18% on D2 and increases to 22% on D8. The product P2 induces a quick increase of 37% increase from D0 to D1 and continues to increase from D2 to D8 to reach 49%. According to these experimental conditions and compared to the blank batch on D8 (TJ8), the following may be concluded:

TABLE 9

| | vs TJ8 | |
|---|---|---|
| | P1 | P2 |
| Corneometry D8 | +22% | +49% |

Overall, under the experimental conditions of this study, the results show that the product according to the present disclosure (P2) shows an increased skin hydration in the stratum corneum on day 8 (D8) as compared to the product P1 and the untreated control T.

Although the invention has been described and illustrated with a certain degree of particularity, it is understood that the present disclosure has been made only by way of example, and that numerous changes in the combination and arrangement of parts, steps and elements can be resorted to by those skilled in the art without departing from the scope of the invention, as hereinafter claimed.

Illustration of Subject Technology as Clauses Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An injectable composition useful for reducing the appearance of superficial depressions in the skin, the composition comprising: a hyaluronic acid (HA) gel comprising a crosslinked HA matrix made with a low molecular weight HA material having a weight average molecular weight of between 0.20 about MDa and about 0.99 MDa; wherein the HA concentration of the composition is less than about 17.0 mg/g; wherein the composition maintains the reduced appearance of superficial depressions in the skin for at least about 3 months from being introduced into the skin.

Clause 2. The composition of Clause 1 wherein the composition maintains the reduced appearance of superficial depressions in the skin for at least about 6 months from being introduced into the skin.

Clause 3. The composition of Clause 1 wherein the composition maintains the reduced appearance of superficial depressions in the skin for at least about 9 months from being introduced into the skin.

Clause 4. The composition of Clause 1 further comprising at least one of mannitol and a vitamin C derivative.

Clause 5. The composition of Clause 4 wherein the mannitol is present in an amount of between about 0.3% to about 0.9% w/w.

Clause 6. The composition of Clause 4 wherein the vitamin C derivative is ascorbic acid 2-glucoside.

Clause 7. The composition of Clause 6 wherein the ascorbic acid 2-glucoside is present in an amount of between about 0.3% to about 0.6% w/w.

Clause 8. The composition of Clause 1 further comprising about 0.9% w/w mannitol and about 0.6% w/w ascorbic acid 2-glucoside.

Clause 9. The composition of Clause 1 wherein the weight average molecular weight of the low molecular weight HA material is between about 400,000 Da and about 800,000 Da.

Clause 10. The composition of Clause 1 wherein the crosslinked HA matrix is crosslinked with a crosslinking agent selected from the group consisting of 1,4-butanediol diglycidyl ether (BDDE), 1,4-bis(2,3-epoxypropoxy)butane, 1,4-bisglycidyloxybutane, 1,2-bis(2,3-epoxypropoxy)ethylene and 1-(2,3-epoxypropyl)-2,3-epoxycyclohexane.

Clause 11. The composition of Clause 1 wherein the HA concentration is about 10.0 mg/g to about 14.0 mg/g.

Clause 12. The composition of Clause 1 wherein the HA concentration is about 12.0 mg/g.

Clause 13. An injectable composition useful for reducing the appearance of superficial depressions in the skin or for improving skin quality, the composition comprising: a hyaluronic acid (HA) gel comprising a crosslinked HA matrix; at least one of a mannitol and a Vitamin C derivative; wherein the HA concentration of the composition is less than about 17.0 mg/g; wherein the composition maintains the reduced appearance of superficial depressions in the skin or the improved skin quality for at least about 3 months from being introduced into the skin.

Clause 14. The composition of Clause 13 wherein the composition maintains the reduced appearance of superficial depressions in the skin or the improved skin quality for at least about 6 months from being introduced into the skin.

Clause 15. The composition of Clause 13 wherein the composition maintains the reduced appearance of superficial depressions in the skin or the improved skin quality for at least about 9 months from being introduced into the skin.

Clause 16. The composition of Clause 13 wherein the mannitol is present in an amount of between about 0.3% to about 0.9% w/w.

Clause 17. The composition of Clause 13 wherein the vitamin C derivative is ascorbic acid 2-glucoside.

Clause 18. The composition of Clause 17 wherein the ascorbic acid 2-glucoside is present in an amount of between about 0.3% to about 0.6% w/w.

Clause 19. The composition of Clause 13 wherein the at least one of a mannitol and a Vitamin C derivative comprises both mannitol present at about 0.9% w/w and a Vitamin C derivative present at about 0.6% w/w.

Clause 20. The composition of Clause 19 wherein the Vitamin C derivative is ascorbic acid 2-glucoside.

Clause 21. The composition of Clause 13 wherein the HA concentration is about 10.0 mg/g to about 14.0 mg/g.

Clause 22. The composition of Clause 13 wherein the HA concentration is about 12.0 mg/g.

Clause 23. A method of improving at least one of texture, hydration and elasticity of skin, the method comprising; treating an area of skin by introducing into a skin region, in a single treatment session, multiple, spaced apart injections of a composition comprising a hyaluronic acid (HA) gel containing crosslinked HA; wherein the HA concentration of the composition is less than about 17.0 mg/g; wherein the treated skin maintains at least one of an improved texture, hydration and elasticity due to the treatment for at least about 3 months.

Clause 24. The method of Clause 23 wherein the treated skin maintains the at least one of an improved texture, hydration and elasticity due to the treatment for at least about 6 months.

Clause 25. The method of Clause 23 wherein the treated skin maintains the at least one of an improved texture, hydration and elasticity due to the treatment for at least about 12 months.

Clause 26. The method of Clause 23 wherein the HA concentration is about 10.0 mg/g to about 14.0 mg/g.

Clause 27. The method of Clause 23 wherein the HA concentration is about 12.0 mg/g.

Clause 28. The method of Clause 23 wherein the injections are spaced apart by a distance of between about 5 mm to about 20 mm.

Clause 29. The method of Clause 23 wherein the injections are introduced in an amount of about 5 µL to about 100 µL per injection.

Clause 30. The method of Clause 23 wherein the treatment takes no longer than about 45 minutes.

Clause 31. The method of Clause 23 wherein the injections are delivered through a needle having a gauge of from 28 G to 33 G.

Clause 32. The method of Clause 23 wherein the composition further comprising at least one of mannitol and a vitamin C derivative.

Clause 33. The method of Clause 23 wherein the mannitol is present in an amount of between about 0.3% and about 0.9% w/w.

Clause 34. The method of Clause 23 wherein the vitamin C derivative is ascorbic acid 2-glucoside.

Clause 35. The method of Clause 34 wherein the ascorbic acid 2-glucoside is present in an amount of between about 0.3% and about 0.6% % w/w.

Clause 36. A method of increasing at least one of smoothness, hydration, and elasticity in skin comprising; introducing, into a skin region at a depth of between about 0.5 to about 4.0 mm or about 0.5 to about 5.0 mm, in a single treatment session, multiple, spaced apart injections of a composition comprising a hyaluronic acid (HA) gel containing BDDE-crosslinked HA and uncrosslinked HA; wherein the injections are introduced in an amount of about 5 μL to about 100 μL per injection; wherein the injections are delivered through a needle having a gauge of from 28 G to 33 G; wherein the injections spaced apart by a distance of between about 5 mm to about 20 mm; and wherein the skin region maintains an increased smoothness, hydration, and/or elasticity due to the treatment for at least about 6 months.

Clause 37. The method of Clause 36 wherein the composition further comprises at least one of mannitol and a vitamin C derivative.

Clause 38. A composition for increasing at least one of smoothness, hydration, and elasticity in skin comprising: a hyaluronic acid (HA) gel comprising a crosslinked HA matrix made with a low molecular weight HA material having a weight average molecular weight of between about 400,000 Da and about 800,000 Da; wherein the HA concentration of the composition is from about 10.0 mg/g to about 14.0 mg/g; and wherein the composition maintains the increased smoothness, hydration, and/or elasticity due to the treatment for at least about 6 months from being introduced into the skin in a single treatment session comprising multiple, spaced apart injections of the composition in which the injections are introduced in an amount of about 5 μL to about 100 μL per injection, delivered through a needle having a gauge of from 28 G to 33 G and are spaced apart by a distance of between about 5 mm to about 20 mm.

Clause 39. The composition of Clause 38 wherein the composition further comprises at least one of mannitol and a vitamin C derivative.

What is claimed is:

1. A method of improving skin smoothness, skin hydration, or skin elasticity on a face or neck of a patient, the method comprising administering to the face, neck, or décolletage of the patient injections of a composition comprising a hyaluronic acid (HA) gel, wherein:
   (i) the HA gel comprises a crosslinked HA matrix made with more than 50% by weight, based on a total weight of the HA material, of a low molecular weight HA material having a weight average molecular weight between 400,000 Da and 800,000 Da;
   (ii) the HA concentration of the composition is 10 mg/g to 12 mg/g;
   (iii) the crosslinked HA matrix is crosslinked with a crosslinking agent selected from the group consisting of 1,4-butanediol diglycidyl ether, 1,2-bis(2,3-epoxypropoxy)ethylene, and 1-(2,3-epoxypropyl)-2,3-epoxycyclohexane;
   (iv) the composition does not include a vitamin; and
   (v) the injections are spaced apart by a distance of between about 2 mm to about 20 mm;
   thereby improving skin smoothness, skin hydration, or skin elasticity on the face, neck, or décolletage of the patient.

2. The method of claim 1, wherein the injections are spaced apart by a distance of between about 2 mm to about 15 mm.

3. The method of claim 1, wherein the injections are spaced apart by a distance of between about 2 mm to about 5 mm.

4. The method of claim 1, wherein the injections are spaced apart by a distance of between about 5 mm to about 10 mm.

5. The method of claim 1, wherein the crosslinked HA matrix made is with at least 70% by weight, based on the total weight of the HA material, of the low molecular weight HA material.

6. The method of claim 1, wherein the crosslinked HA matrix made is with at least 90% by weight, based on the total weight of the HA material, of the low molecular weight HA material.

7. The method of claim 1, wherein the crosslinked HA matrix is with: (a) the low molecular weight HA material and (b) a high molecular weight HA material having a weight average molecular weight from about 1.5 mDa to about 3.0 MDa.

8. The method of claim 1, wherein the injections are intradermal injections.

9. The method of claim 1 for improving skin smoothness on the face of the patient.

10. A method of treating superficial skin depressions on a face, neck, or décolletage of a patient, the method comprising administering to the face, neck, or décolletage of the patient injections of a composition comprising a hyaluronic acid (HA) gel, wherein:
    (i) the HA gel comprises a crosslinked HA matrix made with more than 50% by weight, based on a total weight of the HA material, of a low molecular weight HA material having a weight average molecular weight between 400,000 Da and 800,000 Da;
    (ii) the HA concentration of the composition is 10 mg/g to 12 mg/g;
    (iii) the crosslinked HA matrix is crosslinked with a crosslinking agent selected from the group consisting of 1,4-butanediol diglycidyl ether, 1,2-bis(2,3-epoxypropoxy)ethylene, and 1-(2,3-epoxypropyl)-2,3-epoxycyclohexane;
    (iv) the composition does not include a vitamin; and
    (v) the injections are spaced apart by a distance of between about 2 mm to about 15 mm;
    thereby treating superficial skin depressions on the face, neck, or décolletage of the patient.

11. The method of claim 10, wherein the injections are spaced apart by a distance of between about 2 mm to about 5 mm.

12. The method of claim 10, wherein the injections are spaced apart by a distance of between about 5 mm to about 10 mm.

13. The method of claim 10, wherein the crosslinked HA matrix made is with at least 70% by weight, based on the total weight of the HA material, of the low molecular weight HA material.

14. The method of claim 10, wherein the crosslinked HA matrix made is with at least 90% by weight, based on the total weight of the HA material, of the low molecular weight HA material.

15. The method of claim 10, wherein the crosslinked HA matrix is with: (a) the low molecular weight HA material and (b) a high molecular weight HA material having a weight average molecular weight from about 1.5 mDa to about 3.0 MDa.

16. The method of claim 10, wherein the injections are intradermal injections.

17. A method of improving skin smoothness on a face of a patient, the method comprising administering to the face of the patient intradermal injections of a composition comprising a hyaluronic acid (HA) gel, wherein:
- (i) the HA gel comprises a crosslinked HA matrix made with at least 70% by weight, based on a total weight of the HA material, of a low molecular weight HA material having a weight average molecular weight between 400,000 Da and 800,000 Da;
- (ii) the HA concentration of the composition is 12 mg/ml;
- (iii) the crosslinked HA matrix is crosslinked with 1,4-butanediol diglycidyl ether;
- (iv) the composition does not include a vitamin; and
- (v) the injections are spaced apart by a distance of between about 2 mm to about 10 mm;

thereby improving skin smoothness on the face of the patient.

18. The method of claim 17, wherein the injections are spaced apart by a distance of between about 2 mm to about 5 mm.

19. The method of claim 17, wherein the injections are spaced apart by a distance of between about 5 mm to about 10 mm.

20. The method of claim 17, wherein the crosslinked HA matrix made is with at least 90% by weight, based on the total weight of the HA material, of the low molecular weight HA material.

21. The method of claim 17, wherein the crosslinked HA matrix is with: (a) at least 90% by weight, based on the total weight of the HA material, of the low molecular weight HA material, and (b) a high molecular weight HA material having a weight average molecular weight from about 1.5 mDa to about 3.0 MDa.

22. A method for improving skin smoothness on a face of a patient, the method comprising administering via intradermal injection a hyaluronic acid (HA) gel to the face of the patient, wherein said HA gel comprises crosslinked, low-molecular weight HA, has an HA concentration of from about 10 to 17 mg/g and a gel viscosity G" of between about 10 Pa to about 100 Pa when measured at 0.1 Hz, wherein the HA gel does not include a vitamin, and wherein the patient maintains improved skin smoothness for at least 3 months after a single treatment with said intradermal injection.

23. The method of claim 22, wherein said HA gel is administered via a needle having a gauge of from 28 G to 33 G.

24. The method of claim 22, wherein at least 50% w/w of HA in said HA gel is said crosslinked, low-molecular weight HA.

25. The method of claim 22, wherein at least 70% w/w of HA in said HA gel is said crosslinked, low-molecular weight HA.

26. The method of claim 22, wherein at least 90% w/w of HA in said HA gel is said crosslinked, low-molecular weight HA.

27. The method of claim 22, wherein said low-molecular weight HA has a molecular weight of between about 400,000 Da and about 800,000 Da.

28. The method of claim 22, wherein the patient maintains improved skin smoothness for at least 6 months after a single treatment with said intradermal injection.

* * * * *

UNITED STATES PATENT AND TRADEMARK OFFICE
CERTIFICATE OF CORRECTION

| | | |
|---|---|---|
| PATENT NO. | : 12,011,500 B2 | Page 1 of 1 |
| APPLICATION NO. | : 17/684248 | |
| DATED | : June 18, 2024 | |
| INVENTOR(S) | : Pierre Lebreton and Olivier Guetta | |

It is certified that error appears in the above-identified patent and that said Letters Patent is hereby corrected as shown below:

On the Title Page

Under Related U.S. Application Data, delete "(60)" and insert --(63)--.

In the Claims

At Column 20, Line 11 of Claim 5, delete "made is" and insert --is made--.

At Column 20, Line 15 of Claim 6, delete "made is" and insert --is made--.

At Column 20, Line 19 of Claim 7, delete "is with" and insert --is made with--.

At Column 20, Line 25 of Claim 9, delete "1" and insert --1,--.

At Column 20, Line 56 of Claim 13, delete "made is" and insert --is made--.

At Column 20, Line 60 of Claim 14, delete "made is" and insert --is made--.

At Column 20, Line 64 of Claim 15, delete "is with" and insert --is made with--.

At Column 21, Line 27 of Claim 20, delete "made is" and insert --is made--.

At Column 21, Line 31 of Claim 21, delete "is with" and insert --is made with--.

Signed and Sealed this
Twenty-fifth Day of February, 2025

Coke Morgan Stewart
*Acting Director of the United States Patent and Trademark Office*